US012774337B2

(12) United States Patent
Wang et al.

(10) Patent No.: US 12,774,337 B2
(45) Date of Patent: Oct. 27, 2026

(54) ANTI-FGFR2b ANTIBODIES

(71) Applicant: DIZAL PHARMACEUTICAL CO., LTD., Wuxi (CN)

(72) Inventors: Mei Wang, Shanghai (CN); Qiuli Guo, Shanghai (CN); Yu Bai, Shanghai (CN); Zhenfan Yang, Shanghai (CN); Xiaolin Zhang, Shanghai (CN)

(73) Assignee: DIZAL PHARMACEUTICAL CO., LTD., Wuxi (CN)

( * ) Notice: Subject to any disclaimer, the term of this patent is extended or adjusted under 35 U.S.C. 154(b) by 1037 days.

(21) Appl. No.: 17/788,729

(22) PCT Filed: Dec. 23, 2020

(86) PCT No.: PCT/CN2020/138580
§ 371 (c)(1),
(2) Date: Jun. 23, 2022

(87) PCT Pub. No.: WO2021/129655
PCT Pub. Date: Jul. 1, 2021

(65) Prior Publication Data

US 2023/0055566 A1 Feb. 23, 2023

(30) Foreign Application Priority Data

Dec. 24, 2019 (WO) ................ PCT/CN2019/127902

(51) Int. Cl.

| | |
|---|---|
| ***C07K 16/28*** | (2006.01) |
| ***A61K 47/68*** | (2017.01) |
| ***A61P 1/00*** | (2006.01) |
| ***A61P 35/00*** | (2006.01) |
| *A61K 39/00* | (2006.01) |

(52) U.S. Cl.
CPC .... *C07K 16/2863* (2013.01); *A61K 47/68031* (2023.08); *A61K 47/6849* (2017.08); *A61P 1/00* (2018.01); *A61P 35/00* (2018.01); *A61K 2039/505* (2013.01); *C07K 2317/24* (2013.01); *C07K 2317/33* (2013.01); *C07K 2317/41* (2013.01); *C07K 2317/52* (2013.01); *C07K 2317/565* (2013.01); *C07K 2317/732* (2013.01); *C07K 2317/77* (2013.01); *C07K 2317/92* (2013.01)

(58) Field of Classification Search
CPC ............ C07K 16/2863; C07K 2317/24; C07K 2317/33; C07K 2317/41; C07K 2317/52; C07K 2317/565; C07K 2317/732; C07K 2317/76; C07K 2317/77; C07K 2317/92; A61K 47/6849; A61K 2039/505; A61K 2039/585
See application file for complete search history.

(56) References Cited

U.S. PATENT DOCUMENTS

| | | | |
|---|---|---|---|
| 2007/0071675 | A1 | 3/2007 | Wu et al. |
| 2014/0308201 | A1 | 10/2014 | Batt et al. |
| 2017/0145103 | A1 | 5/2017 | Pierce et al. |
| 2023/0055566 | A1 | 2/2023 | Wang et al. |

FOREIGN PATENT DOCUMENTS

| | | | |
|---|---|---|---|
| JP | 2008501302 | A | 1/2008 |
| JP | 2015505850 | A | 2/2015 |
| JP | 2016527273 | A | 9/2016 |
| JP | 2018531278 | A | 10/2018 |
| JP | 2018538274 | A | 12/2018 |
| RU | 2698061 | C2 | 8/2019 |
| WO | 0177342 | A1 | 10/2001 |
| WO | 2015017600 | A1 | 2/2015 |
| WO | 2017091429 | A1 | 6/2017 |
| WO | 2018095932 | A1 | 5/2018 |
| WO | 2018/129451 | A2 | 7/2018 |
| WO | 2021129655 | A1 | 7/2021 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Murphy et al., Journal of Immunological Methods, 2018, 463: 127-133.*
Shen J. et al., Single variable domain-IgG fusion: a novel recombinant approach to Fc domain-containing bispecific antibodies, Journal of Biological Chemistry, 2006, V. 281, N. 16, p. 10706-10714, c. 10713.
Torres M. et al., The immunoglobulin constant region contributes to affinity and specificity, Trends in immunology, 2008, V. 29, N. 2, p. 91-97, c.93-94.
Haipeng Lei and Chu-Xia Deng, Fibroblast Growth Factor Receptor 2 Signaling in Breast Cancer, Int. J. Biol. Sci., 2017; 13(9): 1163-1171.
Office Action with Search Report for the counterpart Russian Patent application 2022113088, Apr. 15, 2024
Ornitz et al., Receptor Specificity of the Fibroblast Growth Factor Family, The Journal of Biological Chemistry, vol. 271, No. 25, (Jun. 21, 1996), pp. 15292-15297.
UniProtKB P21802 and isoforms P21802-1 to P21802-23 for sequence of human FGFR2 and its isoforms, Jan. 28, 2026.
UniProtKB P11362 and isoforms P11362-1 to P11362-21 for sequence of human FGFR1 and its isoforms, Jan. 28, 2026
Miki et al., Determination of ligand-binding specificity by alternative splicing: Two distinct growth factor receptors encoded by a single gene, Proc. Natl. Acad. Sci. USA, vol. 89, (Jan. 1, 1992), pp. 246-250.

(Continued)

*Primary Examiner* — Hong Sang
(74) *Attorney, Agent, or Firm* — Junhe Law Office P.C.; Zhaohui Wang

(57) ABSTRACT

The present disclosure provides anti-FGFR2b antibodies or antigen-binding fragments thereof, isolated polynucleotides encoding the same, pharmaceutical compositions comprising the same, and the uses thereof.

19 Claims, 5 Drawing Sheets

Specification includes a Sequence Listing.

(56) References Cited

OTHER PUBLICATIONS

Ishiwata et al., Characterization of Keratinocyte Growth Factor and Receptor Expression in Human Pancreatic Cancer, American Journal of Pathology, vol. 153, No. 1, (Jul. 1, 1998), pp. 213-222.
Cho et al., Enhanced Expression of Keratinocyte Growth Factor and Its Receptor Correlates with Venous Invasion in Pancreatic Cancer, The American Journal of Pathology, vol. 170, No. 6, (Jun. 1, 2007), pp. 1964-1974.
Kunii et al., FGFR2-Amplified Gastric Cancer Cell Lines Require FGFR2 and Erbb3 Signaling for Growth and Survival, Cancer Res., vol. 68, No. 7, (Apr. 1, 2008), pp. 2340-2348, 3549.
Nakamura et al., A Novel Molecular Targeting Compound as K-samll/FGF-R2 Phosphorylation Inhibitor, Ki23057, for Scirrhous Gastric Cancer, Gastroenterology, vol. 131, (Aug. 22, 2006), pp. 1530-1541.
Steele et al., Ligands to FGF receptor 2-IIIb induce proliferation, motility, protection from cell death and cytoskeletal rearrangements in epithelial ovarian cancer cell lines, Growth Factors, vol. 24, No. 1, (Mar. 31, 2006), pp. 45-53.
Finch et al., Keratinocyte Growth Factor Expression and Activity in Cancer: Implications for Use in Patients With Solid Tumors, Journal of the National Cancer Institute, vol. 98, No. 12, (Jun. 21, 2006), pp. 812-824.
Moffa et al., Transforming Potential of Alternatively Spliced Variants of Fibroblast Growth Factor Receptor 2 in Human Mammary Epithelial Cells, Mol Cancer Res., vol. 2, No. 11, (Nov. 1, 2004), pp. 643-652.
Freier et al., Recurrent FGFR1 amplification and high FGFR1 protein expression in oral squamous cell carcinoma (OSCC), Oral Oncology, vol. 43, (Jun. 27, 2006), pp. 60-66.
Turner et al., FGFR1 Amplification Drives Endocrine Therapy Resistance and Is a Therapeutic Target in Breast Cancer, Cancer Res., vol. 70, No. 5, (Feb. 23, 2010), pp. 2085-2094.
Ishizuka et al., Gene amplification profiling of esophageal squamous cell carcinomas by DNA array CGH, Biochemical and Biophysical Research Communications, vol. 296, (Aug. 9, 2002), pp. 152-155.
Gorringe et al., High-Resolution Single Nucleotide Polymorphism Array Analysis of Epithelial Ovarian Cancer Reveals Numerous Microdeletions and Amplifications, Clin Cancer Res., vol. 13, No. 16, (Aug. 15, 2007), pp. 4731-4739.
Simon et al., High-Throughput Tissue Microarray Analysis of 3p25 (RAF1) and 8p12 (FGFR1) Copy Number Alterations in Urinary Bladder Cancer, Cancer Res., vol. 61, (Jun. 1, 2001), pp. 4514-4519.
Edwards et al., Gene Amplifications Associated with the Development of Hormone-Resistant Prostate Cancer, Clinical Cancer Research, vol. 9, (Nov. 1, 2003), pp. 5271-5281.
Dutt et al., Inhibitor-Sensitive FGFR1 Amplification in Human Non-Small Cell Lung Cancer, PLoS One, vol. 6, Issue. 6, (Jun. 7, 2011), e20351 pp. 1-10.
Weir et al., Characterizing the cancer genome in lung adenocarcinoma, Nature, vol. 450, (Dec. 6, 2007), pp. 893-898.
Weiss et al., Frequent and Focal FGFR1 Amplification Associates with Therapeutically Tractable FGFR1 Dependency in Squamous Cell Lung Cancer, Science Translational Medicine, vol. 2, Issue 62, (Dec. 15, 2010), 62ra93 pp. 1-7.
The international search report of PCT application No. PCT/CN2020/138580, issued on Mar. 30, 2021.
The Office Action for the counterpart Canadian patent application 3,160,810, mailed on Jun. 1, 2026.

* cited by examiner

AIQLTQSPSSLSASVGDRVTITCSASSGLSYMSWYQQKPGKAPKLLIYDTSNLASGV
PSRFSGSGSGTDFTLTISSLQPEDFATYYCQQWSSYPYTFGQGTKLEIKRTVAAPSV
FIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC (SEQ ID NO: 20)

FIGURE 1A

EVQLVQSGAEVKKPGASVKVSCKASGYTFTNYWMHWVRQAPGQGLEWMGAIYP
ENRDINYNQKFKGRVTLTRDTSISTAYMELSRLRSDDTAVYYCTSRGDYWGQGTT
VTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSP
GK (SEQ ID NO: 21)

FIGURE 1B

| hFGFR2b | | | |
|---|---|---|---|
| Ab | ka (1/Ms) | kd (1/s) | KD (M) |
| FPA144 | 1.035E+05 | 7.766E-05 | 7.504E-10 |
| 21c | 9.134E+04 | 2.460E-05 | 2.693E-10 |
| hu21-21 | 9.795E+04 | 2.447E-05 | 2.498E-10 |
| afhu21-26 | 1.157E+05 | 5.584E-05 | 4.825E-10 |
| **hFGFR1b** | | | |
| Ab | ka (1/Ms) | kd (1/s) | KD (M) |
| FPA144 | 3.32E+04 | 7.46E-03 | 2.25E-07 |
| 21c | 6.38E+04 | 2.35E-04 | 3.69E-09 |

FIGURE 2

ANTI-FGFR2b ANTIBODIES

SEQUENCE LISTING

This application contains a sequence listing, which has been submitted electronically as a .xml file and is herein incorporated by reference in its entirety. Said .xml file, created on Mar. 25, 2026, is named "070542-8006US01" and is 21,770 bytes in size.

FIELD OF THE INVENTION

The present disclosure generally relates to novel anti-human FGFR2b antibodies.

BACKGROUND

Fibroblast growth factor receptors (FGFR) are transmembrane tyrosine kinases which are encoded by four structurally related genes (FGFR1 to FGFR4). The FGFRs are characterized by multiple alternative splicing of their mRNAs, leading to a variety of isoforms (Ornitz et al, J. Biol. Chem. 271:15292, 1996; see also UniProtKB P21802 and isoforms P21802-1 to P21802-23 for sequence of human FGFR2 and its isoforms; UniProtKB P11362 and isoforms P11362-1 to P11362-21 for sequence of human FGFR1 and its isoforms). FGFRs have common structural features which consist of an extracellular ligand-binding section composed of different Ig-like domains (a isoform contains all three Ig-like domains D1, D2, and D3; B isoform contains only the two Ig-like domains D2 and D3 domains but without D1), a transmembrane domain, and an intracellular tyrosine kinase catalytic domain. FGFs bind to the receptors primarily through regions in D2 and D3 of the receptors. In FGFR1-FGFR3, all forms contain the first half of D3, the isoforms containing only the first half of D3 are denoted as IIIa forms, while two alternative exons can be utilized for the second half of D3, leading to IIIb and IIIc forms. For example, in FGFR-1, alternative splicing of the exon encoding the third Ig-like domain produces the FGFRIIIIb or FGFRIIIIc (or just FGFR1b and FGFRIc) splice forms, which have distinct ligand-binding preferences. For FGFR2, these forms are respectively denoted as FGFR2IIIb and FGFR2IIIc (or just FGFR2b and FGFR2c). FGFR2b is produced only in cells of epithelial origin, and FGFR2c only in mesenchymal cells. The FGFR2b form of FGFR2 is a high affinity receptor for FGF1 and is the specific receptor for the KGF family members (e.g., FGF 10, FGF22, and especially FGF7); whereas FGFR2c binds both FGF1 and FGF2 well but does not bind the KGF family members (Miki et al., Proc. Natl. Acad. Sci. USA 89:246, 1992).

The FGFs upon binding to the FGFRs mediate a variety of responses in various cell types including proliferation, migration and differentiation, especially during embryonic development (Ornitz et al., J. Biol. Chem. 271:15292, 1996), and in the adult are involved in tissue homeostasis and repair. KGF (FGF7) and KGFR (FGFR2IIIb) are found involved in various types of cancers such as pancreatic cancer, gastric cancer, ovarian cancer and breast cancer. FGF7 and FGFR2b are overexpressed in pancreatic cancer (Ishiwata et al., Am. J. Pathol. 153:213, 1998), and their co-expression correlates with poor prognosis (Cho et al., Am. J. Pathol. 170:1964, 2007). Amplification and overexpression of FGFR2 is strongly associated with the undifferentiated, diffuse type of gastric cancer, which has a particularly poor prognosis, and inhibition of the FGFR2 activity by small molecule compounds potently inhibited proliferation of such cancer cells (Kunii et al., Cancer Res. 68:2340, 2008; Nakamura et al., Gastroenterol. 131:1530, 2006). FGFR2b ligands FGF1, FGF7 and FGF10 induced proliferation, motility and protection form cell death in EOC cell lines (Steele et al., Growth Factors 24:45, 2006), suggesting that FGFR2b may contribute to the malignant phenotype in ovarian cancer. FGFR2b is highly expressed in about 5% of breast cancer (Finch and Rubin 2006) and mediates signaling cascades via MAPK and PI3K (Moffa, Tannheimer et al. 2004). Frequent activating FGFR2 mutations (e.g., S252W) are also discovered to be associated with various cancers.

Amplification or activation of FGFR1 has been reported in many cancers including oral squamous cell carcinoma (Freier et al., Oral Oncol. 43 (1):60-6, 2007), breast cancer (Turner et al., Cancer Res. 1; 70 (5):2085-94, 2010), esophageal squamous cell carcinoma (Ishizuka et al., Biochem Biophys Res Commun. 9; 296 (1):152-5, 2002), ovarian cancer (Gorringe et al., Clin Cancer Res. 15; 13 (16):4731-9, 2007), bladder cancer (Simon et al., Cancer Res. 1; 61 (11):4514-9, 2001), prostate cancer (Edwards et al., Clin Cancer Res. 1; 9 (14):5271-81 2003), and lung cancer, predominantly in the squamous subtype (Dutt et al., PLOS One. 6(6):e20351, 2011; Weir et al., Nature. 6; 450 (7171): 893-8, 2007; Weiss et al., Sci Transl Med. 15; 2 (62):62ra93, 2010).

There is a significant need for novel anti-FGFR2b antibodies. In particular, it is believed that no antibodies have been reported to be capable of binding to both FGFR2b and FGFR1b.

SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

The present disclosure provides novel monoclonal anti-FGFR2b antibodies, amino acid and nucleotide sequences thereof, and uses thereof.

In one aspect, the present disclosure provides an isolated anti-FGFR2b antibody, comprising: 1, 2 or 3 heavy chain complementarity determining region (CDR) sequences selected from the group consisting of: SEQ ID NOs: 1, 3, 5 and 7; and/or 1, 2 or 3 light chain CDR sequences selected from the group consisting of: SEQ ID NOs: 2, 4 and 6, wherein the antibody is capable of specifically binding to both FGFR2b and FGFR1b. In some embodiments, the antibody provided herein does not have detectable binding affinity to FGFR2c.

In some embodiments, the antibody provided herein comprises: a heavy chain CDR3 of SEQ ID NO: 5, and/or a light chain CDR3 of SEQ ID NO: 6. In some embodiments, the antibody provided herein comprises: a heavy chain variable region ($V_H$) having 1, 2 or 3 heavy chain CDR sequences selected from the group consisting of: SEQ ID NOs: 1, 3, 5 and 7, and/or a light chain variable region ($V_L$) having 1, 2 or 3 light chain CDR sequences selected from the group consisting of: SEQ ID NOs: 2, 4 and 6. In some embodiments, the antibody provided herein comprises: a heavy chain variable region ($V_H$) comprising SEQ ID NOs: 1, 3, and 5, and/or a light chain variable region ($V_L$) comprising SEQ ID NOs: 2, 4 and 6. In some embodiments, the antibody provided herein comprises: a heavy chain variable region ($V_H$) comprising SEQ ID NOs: 1, 7, and 5, and/or a light chain variable region ($V_L$) comprising SEQ ID NOs: 2, 4 and 6.

In some embodiments, the antibody provided herein comprises: a heavy chain variable region comprising: SEQ ID NOs: 8, 12, or 16 or a homologous sequence thereof having at least 80% sequence identity to SEQ ID NOs: 8, 12, or 16. In some embodiments, the antibody provided herein comprises: a light chain variable region comprising: SEQ ID NOs: 10 or 14 or a homologous sequence thereof having at least 80% sequence identity to SEQ ID NOs: 10 or14. In some embodiments, the antibody provided herein comprises: a heavy chain variable region comprising SEQ ID NO: 8 and a light chain variable region comprising SEQ ID NO: 10. In some embodiments, the antibody provided herein comprises: a heavy chain variable region comprising SEQ ID NO: 12 and a light chain variable region comprising SEQ ID NO: 14. In some embodiments, the antibody provided herein comprises: a heavy chain variable region comprising SEQ ID NO: 16 and a light chain variable region comprising SEQ ID NO: 10.

In some embodiments, the antibody provided herein further comprises one or more amino acid residue substitutions or modifications yet retains specific binding affinity to FGFR2b and/or to FGFR1b. In some embodiments, the at least one of the substitutions or modifications is in one or more of the CDR sequences, and/or in one or more of the $V_H$ and $V_L$ sequences, or in one or more of the $V_H$ and $V_L$ sequences but outside any of the CDR sequences.

In some embodiments, the antibody provided herein further comprises an immunoglobulin constant region, optionally a constant region of human immunoglobulin, preferably a constant region of human IgG, more preferably a constant region of human IgG1.

In some embodiments, the antibody provided herein further comprises within its constant region one or more modifications which: a) introduces or removes a glycosylation site, b) introduces a free cysteine residue, c) enhances binding to an activating Fc receptor, and/or d) enhances antibody-dependent cellular cytotoxicity (ADCC).

In some embodiments, the antibody provided herein is glyco-engineered. In some embodiments, the antibody provided herein is afucosylated. In some embodiments, the afucosylated antibody provided herein lacks fucose at Asn297. In some specific embodiments, the glyco-engineered antibody exhibits enhanced ADCC activity than its non-engineered counterpart. In some embodiments, the enhanced ADCC is characterized in at least 10%, 15%, 20%, 25%, 30%, 35%, 40%, 45%, 50%, 60%, 65%, 70%, or 75% higher lysis of FGFR2b expressing cell.

In some embodiments, the antibody provided herein is a chimeric antibody. In some other embodiments, the antibody provided herein is a humanized antibody.

In some embodiments, the antibody provided herein is linked to one or more conjugate moieties. In certain embodiments, the conjugate moiety comprises a therapeutic agent, a radioactive isotope, a detectable label, a pharmacokinetic modifying moiety, or a purifying moiety. In some embodiments, the conjugate moiety is covalently attached either directly or via a linker.

In another aspect, the present disclosure further provides isolated antibodies or antigen binding fragment thereof, which competes for binding to FGFR2b and/or FGFR 1b with the antibody described above.

In one aspect, the present disclosure provides an isolated polynucleotide encoding the antibody provided herein. In some embodiments, the isolated polynucleotide comprises a nucleotide sequence selected from a group consisting of: SEQ ID NOs: 9, 11, 13, 15, or 17, and a homologous sequence thereof having at least 80% sequence identity to SEQ ID NOs: 9, 11, 13, 15, or 17. In some embodiments, the homologue sequence encodes the same protein as encoded by SEQ ID NOs: 9, 11, 13, 15, or 17.

In another aspect, the present disclosure provides an expression vector comprising the isolated polynucleotide provided herein.

In yet another aspect, the present disclosure provides a host cell comprising the expression vector of the present disclosure.

In yet another aspect, the present disclosure provides a method of producing the antibody provided herein. In some embodiments, the method comprises culturing the host cell of the present disclosure under the condition at which the expression vector of the present disclosure is expressed. In some embodiments, the method further comprises purifying the antibody produced by the host cell.

In yet another aspect, the present disclosure provides a pharmaceutical composition comprising the antibody provided herein, and a pharmaceutically acceptable carrier.

In another aspect, the present disclosure provides a method of treating a FGFR2b- and/or FGFR1b-related disease or condition in a subject, comprising administering a therapeutically effective amount of the antibody or the pharmaceutical composition of the present disclosure.

In some embodiments, the disease or condition is cancer, and optionally the cancer is characterized in expressing or over-expressing FGFR2b and/or FGFR1b.

In some embodiments, the administration is via oral, nasal, intravenous, subcutaneous, sublingual, or intramuscular administration. In some embodiments, the subject is human.

In another aspect, the present disclosure provides a method of detecting the presence or amount of FGFR2b and/or FGFR1b in a sample, comprising contacting the sample with the antibody of the present disclosure, and determining the presence or the amount of FGFR2b and/or FGFR1b in the sample.

In another aspect, the present disclosure provides a method of diagnosing a FGFR2b- and/or FGFR1b-related disease or condition in a subject, comprising: a) contacting a sample obtained from the subject with the antibody of the present disclosure; b) determining the presence or amount of FGFR2b and/or FGFR1b in the sample; c) correlating the presence or the amount of FGFR2b and/or FGFR1b to existence or status of the FGFR2b- and/or FGFR1b-related disease or condition in the subject.

In another aspect, the present disclosure provides methods of prognosing a FGFR2b- and/or FGFR1b-related disease or condition in a subject, comprising: a) contacting a sample obtained from the subject with the antibody of the present disclosure; b) determining the presence or amount of FGFR2b and/or FGFR1b in the sample; c) correlating the presence or the amount of FGFR2b and/or FGFR1b to potential responsiveness of the subject to a FGFR2b and/or a FGFR1b antagonist.

In another aspect, the present disclosure provides use of the antibody of the present disclosure in the manufacture of a medicament for treating a disease or condition that would benefit from modulation of FGFR2b and/or FGFR1b expression in a subject.

In another aspect, the present disclosure provides use of the antibody of the present disclosure in the manufacture of a diagnostic reagent for detecting FGFR2b and/or FGFR1b related disease or condition.

In yet another aspect, the present disclosure provides kits for detecting FGFR2b and/or FGFR1b, comprising the antibody of the present disclosure.

BRIEF DESCRIPTION OF THE DRAWINGS

FIG. 1. Amino acid sequences of the entire Ab hu21-26 (denoted as "hu21-26" in the figures) light chain (A) and heavy chain (B) with the CDRs underlined.

FIG. 2. Biacore binding Kα, Koff, and affinity KD of Ab 21c, Ab hu21-21, and afhu21-26 (respectively denoted as "21c", "hu21-21" and "afhu21-26" in the figures) to human FGFR2b or human FGFR1b with FPA144 as control antibody for reference comparison.

DETAILED DESCRIPTION OF THE INVENTION

Figure 3:
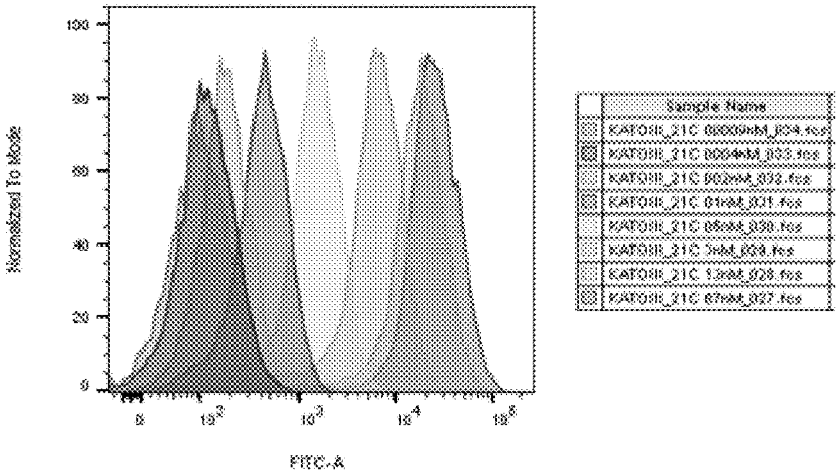
FIG. 3. Flow cytometry of dose-dependent binding of the chimeric Ab 21c to FGFR2b on KATOIII cells.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, bivalent antibody, monovalent antibody, multispecific antibody, bispecific antibody as well as the antigen-binding fragment thereof that binds to a specific antigen. A native intact antibody comprises two heavy (H) chains and two light (L) chains. Mammalian heavy chains are classified as alpha, delta, epsilon, gamma, and mu, each heavy chain consists of a variable region ($V_H$) and a first, second, and third constant region ($C_{H1}$, $C_{H2}$, $C_{H3}$, respectively); mammalian light chains are classified as λ or κ, while each light chain consists of a variable region ($V_L$) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies disclosed herein may be defined or identified by the conventions of Kabat, IMGT, Chothia, or Al-Lazikani (Al-Lazikani, B., Chothia, C., Lesk, A. M., J. Mol. Biol., 273 (4), 927 (1997); Chothia, C. et al., J Mol Biol. December 5; 186 (3):651-63 (1985); Chothia, C. and Lesk, A. M., J.Mol.Biol., 196,901 (1987); Chothia, C. et al., Nature. December 21-28; 342 (6252):877-83 (1989); Kabat E. A. et al., National Institutes of Health, Bethesda, Md. (1991); Marie-Paule Lefranc et al, Developmental and Comparative Immunology, 27:55-77 (2003); Marie-Paule Lefranc et al, Immunome Research, 1 (3), (2005); Marie-Paule Lefranc, Molecular Biology of B cells (second edition), chapter 26, 481-514, (2015)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgAQ1 (alpha1 heavy chain), or IgA2 (alpha2 heavy chain).

The term "antigen-binding fragment" as used herein refers to an antibody fragment formed from a portion of an intact antibody comprising one or more CDRs, or any other antibody fragment that can bind to an antigen but does not comprise an intact native antibody structure. Examples of antigen-binding fragment include, without limitation, a diabody, a Fab, a Fab', a $F(ab')_2$, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), single-chain Fv-Fc antibody (scFv-Fc), an scFv dimer (bivalent diabody), a bispecific antibody, a multispecific antibody, a camelized single domain antibody, a nanobody, a domain antibody, and a bivalent domain antibody. An antigen-binding fragment is capable of binding to the same antigen to which the parent antibody binds.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'. "Fv" with regard to an antibody refers to the smallest fragment of the antibody to bear the complete antigen-binding site. An Fv fragment consists of the variable region of a single light chain bound to the variable region of a single heavy chain.

A "dsFv" refers to a disulfide-stabilized Fv fragment that the linkage between the variable region of a single light chain and the variable region of a single heavy chain is a disulfide bond. In some embodiments, a "(dsFv)$_2$" or "(dsFv-dsFv')" comprises three peptide chains: two $V_H$ moieties linked by a peptide linker (e.g., a long flexible linker) and bound to two $V_L$ moieties, respectively, via disulfide bridges. In some embodiments, dsFv-dsFv' is bispecific in which each disulfide paired heavy and light chain has a different antigen specificity.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85: 5879 (1988)).

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as antibody-dependent cell-mediated cytotoxicity (ADCC), and complement dependent cytotoxicity (CDC), but does not function in antigen binding.

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., J Immunol Methods. December 10; 231 (1-2): 25-38 (1999); Muyldermans S., J Biotechnol. Jun; 74 (4): 277-302 (2001); WO94/04678; WO94/25591; U.S. Pat. No. 6,005,079). Heavy chain antibodies were originally derived from *Camelidae* (camels, dromedaries, and llamas). Although devoid of light chains, camelized antibodies have an authentic antigen-binding repertoire (Hamers-Casterman C. et al., Nature. June 3; 363 (6428):446-8 (1993); Nguyen V K. et al. "Heavy-chain antibodies in Camelidae; a case of evolutionary innovation," Immunogenetics. Apr; 54 (1):39-47 (2002); Nguyen V K. et al. Immunology. May; 109 (1):93-101 (2003)). The variable domain of a heavy chain antibody ("VHH domain") represents the smallest known antigen-binding unit generated by adaptive immune responses (Koch-Nolte F. et al., FASEB J. Nov; 21 (13): 3490-8. Epub 2007 Jun. 15 (2007)).

A "nanobody" refers to an antibody fragment that consists of one VH domain from a heavy chain antibody of a conventional IgG, and two heavy chain constant domains, for example CH2 and CH3.

"Diabodies" or "dAbs" include small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g., Holliger P. et al., Proc Natl Acad Sci USA. July 15; 90 (14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes). In certain embodiments, a "bispecific ds diabody" is a diabody target two different antigens (or epitopes).

In certain embodiments, a "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, a "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human animal such as mouse. In some embodiments, the non-human animal is a mammal, for example, a mouse, a rat, a rabbit, a goat, a sheep, a guinea pig, or a hamster.

The term "humanized" as used herein means that the antibody or antigen-binding fragment comprises CDRs derived from non-human animals, FR regions derived from human, and when applicable, the constant regions are derived from human.

The term "bivalent" as used herein refers to an antibody or an antigen-binding fragment having two antigen-binding sites; the term "monovalent" refers to an antibody or an antigen-binding fragment having only one single antigen-binding site; and the term "multivalent" refers to an antibody or an antigen-binding fragment having multiple antigen-binding sites.

As used herein, a "bispecific" antibody refers to an artificial antibody or an antigen-binding fragment which has fragments derived from two different monoclonal antibodies and is capable of binding to two different epitopes. The two epitopes may present on the same antigen, or they may present on two different antigens.

Unless otherwise specified, the term "FGFR" as used herein encompasses any or all of the fibroblast growth factor receptor family members (FGFR1-FGFR4), and is intended to encompass any form of FGFRs, for example, 1) native unprocessed FGFR molecules, "full-length" FGFR chains or naturally occurring variants of FGFRs, including, for example, allelic variants; 2) any form of FGFR that results from processing in the cell, e.g. different splicing forms, for example, FGFR1b, FGFRIc, FGFR2a, FGFR2b, FGFR2c and the like; or 3) a fragment (e.g., a truncated form, an extracellular/transmembrane domain) or a modified form (e.g. a mutated form, a glycosylated/PEGylated, a His-tag/ immunofluorescence fused form) of FGFR subunit generated through recombinant methods. "FGFR" as used herein can be derived from any vertebrate source, including mammals such as primates (e.g. humans, monkeys) and rodents (e.g., mice and rats).

The term "FGFR2IIIb" and "FGFR2b" are used interchangeably to refer to the subtype IIIb splice form of FGFR2. Exemplary sequences of FGFR2b include *Homo sapiens* (human) FGFR2b protein (e.g., precursor sequence with signal peptide, Genbank accession number: NP_075259.4); *Rattus norvegicus* (Rat) FGFR2b protein (e.g., full sequence, Genbank accession number: NP_001103363.1); *Mus musculus* (mouse) FGFR2b protein (e.g., full sequence, Genbank accession number: NP_963895.2).

"FGFR2IIIc" or "FGFR2c" are used interchangeably to refer to the subtype IIIc splice form of FGFR2. Exemplary sequences of FGFR2c include human FGFR2c protein (e.g., precursor sequence, Genbank accession number: NP_000132.3); *Rattus norvegicus* (Rat) FGFR2c protein (full sequence, Genbank accession number: NP_001103362.1); *Mus musculus* (mouse) FGFR2c protein (full sequence, Genbank accession number: NP_034337.2).

The term "FGFRIIIIb" and "FGFR1b" are used interchangeably to refer to the subtype IIIb splice form of FGFR1. Exemplary sequences of FGFR1b include *Homo sapiens* (human) FGFR1b protein (e.g., precursor sequence with signal peptide, UniProtKB accession number: P11362-19); *Mus musculus* (mouse) FGFR1b protein (e.g., precursor sequence with signal peptide, UniProtKB accession number: P16092-5).

The term "anti-FGFR2b antibody" refers to an antibody that is capable of specifically binding to FGFR2b. In some embodiments, the anti-FGFR2b antibodies provided herein are capable of specifically binding to both FGFR2b and FGFR1b, but does not bind to FGFR2c and FGFRIc or bind less well to FGFR2c and FGFRIc (e.g., the binding affinity to FGFR2c or FGFRIc is at least 10-fold lower than that to FGFR2b or FGFR1b, or at least 50-fold lower, or at least 100-fold lower, or at least 200-fold lower). In some embodiments, the anti-FGFR2b antibodies provided herein do not have detectable binding affinity to FGFR2c.

The term "specific binding" or "specifically binds" as used herein refers to a non-random binding reaction between two molecules, such as for example between an antibody and an antigen. Binding affinity of the antibody and antigen-binding fragment provided herein can be represented by $K_D$ value, which represents the ratio of dissociation rate to association rate ($k_{off}/k_{on}$) when the binding between the antigen and antigen-binding molecule (e.g. the antibody and antigen-binding fragment) reaches equilibrium. The antigen-binding affinity (e.g. KD) can be appropriately determined using suitable methods known in the art, including, for example, Biacore techniques (which is based on surface plasmon resonance technology, see, for example, Murphy, M. et al, Current protocols in protein science, Chapter 19, unit 19.14, 2006), Kinexa techniques (see, for example, Darling, R. J., et al, Assay Drug Dev. Technol., 2 (6):647-657 (2004)), and flow cytometry.

The ability to "compete for binding" as used herein refers to the ability of an antibody or antigen-binding fragment to inhibit the binding interaction between two molecules (e.g. human FGFR2b and an anti-FGFR2b antibody) to any detectable degree (e.g. by at least 85%, or at least 90%, or at least 95%). Those skilled in the art will recognize that it is possible to determine, without undue experimentation, if a given antibody competes for binding to FGFR 2b and/or to FGFR1b with the antibody of present disclosure (e.g., Ab 21, Ab 21c, Ab hu21-21, or Ab hu21-26, defined below).

The term "epitope" as used herein refers to the specific group of atoms or amino acids on an antigen to which an antibody binds.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "homologue" and "homologous" as used herein are interchangeable and refer to nucleic acid sequences (or its complementary strand) or amino acid sequences that have sequence identity of at least 80% (e.g., at least 85%, 88%, 90%, 91%, 92%, 93%, 94%, 95%, 96%, 97%, 98%, or 99%) to another sequences when optimally aligned.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23 (21):2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated polynucleotide sequence" refers to the sequence of an isolated polynucleotide molecule. In certain embodiments, an "isolated antibody" refers to the antibody having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% as determined by electrophoretic methods (such as SDS-PAGE, isoelectric focusing, capillary electrophoresis), or chromatographic methods (such as ion exchange chromatography or reverse phase HPLC).

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

"Antibody-dependent cell-mediated cytotoxicity" and "ADCC" refer to a cell-mediated reaction in which effector cells that express Fc receptors (FcRs) recognize bound antibody or antigen-binding fragment on a target cell and subsequently cause lysis of the target cell. "ADCC activity" refers to the ability of the antibody or antigen-binding fragment which is bound on the target cell to elicit an ADCC reaction as described above.

"Target cells" are cells to which antibodies comprising an Fc region specifically bind, generally via the protein part that is C-terminal to the Fc region. "Effector cells" are leukocytes which express one or more Fc receptors and perform effector functions. Preferably, the cells express at least FcγRIII and perform ADCC effector function. Examples of human leukocytes which mediate ADCC include peripheral blood mononuclear cells (PBMCs), natural killer (NK) cells, monocytes, cytotoxic T cells and neutrophils; with PBMCs and NK cells being preferred. The effector cells may be isolated from a native source thereof, e.g., from blood or PBMCs as is known in the art.

As used herein a "vector" refers to a polynucleotide molecule which enables replicating/cloning of a desired nucleic acid fragment contained therein, or enables expressing of a protein encoded by such desired nucleic acid fragment as introduced into an appropriate cell host. Examples of vectors include both cloning vectors and expression vectors. The term "expression vector" as used herein refers to a vehicle into which a polynucleotide encoding a protein may be operably inserted so as to bring about the expression of that protein. An expression vector may contain a variety of elements for controlling expression, including promoter sequences, transcription initiation sequences, enhancer sequences, selectable elements, and reporter genes. In addition, the vector may contain an origin of replication.

The phrase "host cell" as used herein refers to a cell into which an exogenous polynucleotide and/or an expression vector has been introduced.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

A "FGFR 2b- and/or FGFR 1b-related" disease or condition as used herein refers to any disease or condition that is susceptible to treatment with an FGFR2b modulator and/or an FGFR1b modulator, or is associated with expression or over-expression of FGFR2b and/or FGFR1b. In some embodiments, the FGFR 2b- and/or FGFR 1b-related disease or condition is cancer, and optionally a cancer which is positive for FGFR2b and/or FGFR1b expression or elevated expression.

"Cancer" as used herein refers to any medical condition characterized by malignant cell growth or neoplasm, abnormal proliferation, infiltration or metastasis, and includes both solid tumors and non-solid cancers. As used herein "solid tumor" refers to a solid mass of neoplastic and/or malignant cells. "Non-solid cancer" refers to hematologic malignancies such as leukemia, lymphoma, myeloma and other hematologic malignancies. Examples of cancer or tumor include hematological malignancies (for example, lymphoma, Hodgkin's lymphoma, non-Hodgkin's lymphoma and B-cell lymphoma), oral carcinomas (for example of the lip, tongue or pharynx), tumors in digestive organs (for example esophagus, stomach, small intestine, colon, large intestine, or rectum), peritoneum, liver and biliary passages, pancreas, respiratory system such as larynx or lung (small cell and non-small cell), bone, connective tissue, skin (e.g., melanoma), breast, reproductive organs (fallopian tube, uterus, cervix, testicles, ovary, or prostate), urinary tract (e.g., bladder or kidney), brain and endocrine glands such as the thyroid. In certain embodiments, the cancer is selected from ovarian cancer, endometrial cancer, breast cancer, lung cancer (small cell or non-small cell), bladder cancer, colon cancer, prostate cancer, cervical cancer, colorectal cancer, pancreatic cancer, gastric cancer, esophageal cancer, hepatocellular carcinoma (liver cancer), renal cell carcinoma (kidney cancer), head-and-neck cancer, mesothelioma, melanoma, sarcomas, and brain tumors (e.g., gliomas, such as glioblastomas).

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-FGFR2b Antibodies

The present disclosure provides anti-FGFR2b antibodies comprising one or more (e.g. 1, 2, 3, 4, 5, or 6) CDR sequences of Ab 21. Table 1 shows the CDR sequences of Ab 21. The term "Ab 21" as used herein refers to a mouse monoclonal antibody having a heavy chain variable region of SEQ ID NO: 12, and a light chain variable region of SEQ ID NO: 14. Ab 21 specifically binds to both FGFR2b and FGFR1b.

TABLE 1

CDR amino acid sequences of Ab 21

| | | | |
|---|---|---|---|
| Ab 21 | HCDR1<br>SEQ ID NO: 1<br>NYWMH | HCDR2<br>SEQ ID NO: 3<br>AIYPENGDINYNQKFKG | HCDR3<br>SEQ ID NO: 5<br>RGDY |
| | LCDR1<br>SEQ ID NO: 2<br>SASSGLSYMS | LCDR2<br>SEQ ID NO: 4<br>DTSNLAS | LCDR3<br>SEQ ID NO: 6<br>QQWSSYPYT |

CDRs are known to be responsible for antigen binding, however, it has been found that not all of the 6 CDRs are indispensable or unchangeable. In other words, it is possible to replace or change or modify one or more CDRs in Ab 21, yet substantially retain the specific binding affinity to FGFR, in particular, to FGFR2b and FGFR1b.

In certain embodiments, the anti-FGFR2b antibodies provided herein may comprise one or more modifications or substitutions in one or more CDR regions as provided in Table 1. Such variants retain specific binding affinity to FGFR2b and/or FGFR1b of their parent antibody, but may have one or more improvement in properties such as higher antigen-binding affinity or reduced likelihood of glycosylation.

In certain embodiments, the anti-FGFR2b antibodies provided herein may be modified to remove one or more Asn or Asp hotspots within the CDR regions (or within the variable regions). Such Asn and Asp hotspots may lead to degradation of the antibodies and consequently reduce the stability of the antibodies. Exemplary putative hotspot motifs within the CDR regions include Asn-Gly, Asn-Thr, Asn-Ser, Asn-Asn, Asp-Gly, Asp-Thr, Asp-Ser, Asp-Asp, and Asp-His. In certain embodiments, the HCDR2 of Ab 21 is modified to remove the Asn-Gly (NG) hotspot. In certain embodiments, the modified HCDR2 comprises SEQ ID NO: 7 (AIYPENRDINYNQKFKG).

In certain embodiments, the anti-FGFR2b antibodies provided herein comprise a heavy chain CDR3 sequence of SEQ ID NO: 5, and optionally a light chain CDR3 of SEQ ID NO: 6. The Heavy chain CDR3 region is located at the center of the antigen-binding site, and therefore is believed to make the most contact with antigen and provides the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S. Nature. 302:575-81. (1983)). The diversity in the heavy chain CDR3 is sufficient to produce most antibody specificities (Xu J L, Davis M M. Immunity. 13:37-45 (2000)) as well as desirable antigen-binding affinity (Schier R, etc. J Mol Biol. 263:551-67 (1996)).

In certain embodiments, the anti-FGFR2b antibodies provided herein further comprise suitable framework region (FR) sequences, as long as the antibodies can specifically bind to FGFR2b and/or FGFR1b. The CDR sequences provided in Table 1 are obtained from a mouse antibody, but they can be grafted to any suitable FR sequences of any suitable species such as mouse, human, rat, rabbit, among others, using suitable methods known in the art such as recombinant techniques.

In certain embodiments, the anti-FGFR2b antibodies provided herein are humanized. Exemplary humanized antibodies provided herein include, Ab Hu21-21 and Ab hu21-26.

"Ab hu21-21" as used herein refers to a humanized antibody based on Ab 21, having a heavy chain variable region of SEQ ID NO: 16, and a light chain variable region of SEQ ID NO: 10.

"Ab hu21-26" as used herein refers to a humanized antibody based on Ab 21, having a heavy chain variable region of SEQ ID NO: 8, and a light chain variable region of SEQ ID NO: 10. The heavy chain variable region sequence of Ab hu21-26 (SEQ ID NO: 8) is otherwise identical to that of Ab hu21-21 (SEQ ID NO: 16) except for a G56R mutation, which removes a NG hot spot in HCDR2.

In certain embodiments, the anti-FGFR2b antibodies provided herein further comprise an immunoglobulin constant region, optionally a human immunoglobulin, optionally a human IgG. In some embodiments, an immunoglobulin constant region comprises a heavy chain and/or a light chain constant region. The heavy chain constant region comprises CH1, hinge, and/or CH2-CH3 regions. In certain embodiments, the heavy chain constant region comprises a Fc region. In certain embodiments, the light chain constant region comprises CK or C2.

In certain embodiments, the anti-FGFR2b antibodies provided herein are chimeric antibodies comprising a mouse variable region and a human constant region. "Ab 21c" as used herein refers to a chimeric antibody based on Ab 21, which comprises a mouse heavy chain variable region of SEQ ID NO: 12, and a mouse light chain variable region of SEQ ID NO: 14, fused respectively to human heavy chain constant region and human light chain constant region.

Table 2 and Table 3 show the variable region sequences of the exemplary antibodies.

TABLE 2

| Amino acid sequences of variable regions of the exemplary antibodies | |
|---|---|
| Ab hu21-26 | $V_H$ (SEQ ID NO:8)<br>EVQLVQSGAEVKKPGASVKVSCKASGYTFTNYWMHWVR<br>QAPGQGLEWMGAIYPENRDINYNQKFKGRVTLTRDTSI<br>STAYMELSRLRSDDTAVYYCTSRGDYWGQGTTVTVSS<br><br>$V_L$ (SEQ ID NO: 10)<br>AIQLTQSPSSLSASVGDRVTITCSASSGLSYMSWYQQK<br>PGKAPKLLIYDTSNLASGVPSRFSGSGSGTDFTLTISS<br>LQPEDFATYYCQQWSSYPYTFGQGTKLEIK |
| Ab 21c | $V_H$ (SEQ ID NO: 12)<br>EVQLHQSGTVLARPGASVKMSCKTSGYTFTNYWMHWIK<br>QRPGQGLEWIGAIYPENGDINYNQKFKGKAKLTAVTSA<br>STAYMDLSSLTNEDSAVYYCTSRGDYWGQGTTLTVSS<br><br>$V_L$(SEQ ID NO: 14)<br>QIVLTQSPAIMSASPGEKVTMTCSASSGLSYMSWYQQK<br>PGSSPRLLIYDTSNLASGVPVRFSGSGSGTSYSLTISR<br>MEAEDAATYYCQQWSSYPYTFGGGTKLEIK |
| Ab hu21-21 | $V_H$ (SEQ ID NO: 16)<br>EVQLVQSGAEVKKPGASVKVSCKASGYTFTNYWMHWVR<br>QAPGQGLEWMGAIYPENGDINYNQKFKGRVTLTRDTSI<br>STAYMELSRLRSDDTAVYYCTSRGDYWGQGTTVTVSS<br><br>$V_L$ (SEQ ID NO: 10)<br>AIQLTQSPSSLSASVGDRVTITCSASSGLSYMSWYQQK<br>PGKAPKLLIYDTSNLASGVPSRFSGSGSGTDFTLTISS<br>LQPEDFATYYCQQWSSYPYTFGQGTKLEIK |

TABLE 3

| Nucleotide sequences of variable regions of the exemplary antibodies | |
|---|---|
| Ab hu21-26 | $V_H$: Nucleotide sequence (SEQ ID NO:9)<br>GAGGTGCAGCTGGTGCAGAGCGGCGCCGAGGTGAAGAAGCC<br>CGGCGCCAGCGTGAAGGTGAGCTGCAAGGCCAGCGGCTACA<br>CCTTCACCAACTACTGGATGCACTGGGTGAGGCAGGCCCCCG<br>GCCAGGGCCTGGAGTGGATGGGCGCCATCTACCCCGAGAACA<br>GGGACATCAACTACAACCAGAAGTTCAAGGGCAGGGTGACCC<br>TGACCAGGGACACCAGCATCAGCACCGCCTACATGGAGCTGA<br>GCAGGCTGAGGAGCGACGACACCGCCGTGTACTACTGCACCA<br>GCAGGGGCGACTACTGGGGCCAGGGCACCACCGTGACCGTG<br>AGCAGC<br><br>$V_L$: Nucleotide sequence (SEQ ID NO: 11)<br>GCCATCCAGCTGACCCAGAGCCCCAGCAGCCTGAGCGCCAGC<br>GTGGGCGACAGGGTGACCATCACCTGCAGCGCCAGCAGCGGC<br>CTGAGCTACATGAGCTGGTACCAGCAGAAGCCCGGCAAGGCC<br>CCCAAGCTGCTGATCTACGACACCAGCAACCTGGCCAGCGGC<br>GTGCCCAGCAGGTTCAGCGGCAGCGGCAGCGGCACCGACTTC<br>ACCCTGACCATCAGCAGCCTGCAGCCCGAGGACTTCGCCACC<br>TACTACTGCCAGCAGTGGAGCAGCTACCCCTACACCTTCGGC<br>CAGGGCACCAAGCTGGAGATCAAG |
| Ab 21c | $V_H$: Nucleotide sequence (SEQ ID NO: 13)<br>GAGGTTCAGCTCCACCAGTCTGGGACTGTGCTGGCAAGGCCT<br>GGGGCTTCAGTGAAGATGTCCTGCAAGACTTCTGGCTACACA<br>TTTACCAACTACTGGATGCACTGGATAAAACAGAGGCCTGGA<br>CAGGGTCTGGAATGGATAGGGGCTATTTATCCTGAAAATGGT<br>GATATTAACTACAACCAGAAGTTCAAGGGCAAGGCCAAACTG<br>ACTGCAGTCACATCCGCCAGCACTGCCTACATGGACCTCAGC<br>AGCCTGACAAATGAGGACTCTGCGGTCTATTACTGTACAAGT<br>CGGGGGGACTACTGGGGCCAAGGCACCACTCTCACAGTCTCC<br>TCA<br><br>$V_L$: Nucleotide sequence (SEQ ID NO: 15)<br>CAAATTGTTCTCACCCAGTCTCCAGCAATCATGTCTGCATCT<br>CCAGGGGAGAAGGTCACCATGACCTGCAGTGCCAGCTCAGGT<br>TTAAGTTACATGTCCTGGTACCAGCAGAAGCCAGGATCCTCC<br>CCCAGACTCCTGATTTATGACACATCCAACCTGGCTTCTGGA<br>GTCCCTGTTCGCTTCAGTGGCAGTGGGTCTGGGACCTCTTAC<br>TCTCTCACAATCAGCCGAATGGAGGCTGAAGATGCTGCCACT |

TABLE 3-continued

| Nucleotide sequences of variable regions of the exemplary antibodies | |
|---|---|
| | TATTACTGCCAGCAGTGGAGTAGTTACCCGTACACGTTCGGA<br>GGGGGGACCAAGCTGGAAATAAAA |
| Ab hu21-21 | $V_H$: Nucleotide sequence (SEQ ID NO: 17)<br>GAGGTGCAGCTGGTGCAGAGCGGCGCCGAGGTGAAGAAGCC<br>CGGCGCCAGCGTGAAGGTGAGCTGCAAGGCCAGCGGCTACA<br>CCTTCACCAACTACTGGATGCACTGGGTGAGGCAGGCCCCCG<br>GCCAGGGCCTGGAGTGGATGGGCGCCATCTACCCCGAGAACG<br>GCGACATCAACTACAACCAGAAGTTCAAGGGCAGGGTGACCC<br>TGACCAGGGACACCAGCATCAGCACCGCCTACATGGAGCTGA<br>GCAGGCTGAGGAGCGACGACACCGCCGTGTACTACTGCACCA<br>GCAGGGGCGACTACTGGGGCCAGGGCACCACCGTGACCGTG<br>AGCAGC |
| | $V_L$: Nucleotide sequence (SEQ ID NO: 11)<br>GCCATCCAGCTGACCCAGAGCCCCAGCAGCCTGAGCGCCAGC<br>GTGGGCGACAGGGTGACCATCACCTGCAGCGCCAGCAGCGGC<br>CTGAGCTACATGAGCTGGTACCAGCAGAAGCCCGGCAAGGCC<br>CCCAAGCTGCTGATCTACGACACCAGCAACCTGGCCAGCGGC<br>GTGCCCAGCAGGTTCAGCGGCAGCGGCAGCGGCACCGACTTC<br>ACCCTGACCATCAGCAGCCTGCAGCCCGAGGACTTCGCCACC<br>TACTACTGCCAGCAGTGGAGCAGCTACCCCTACACCTTCGGC<br>CAGGGCACCAAGCTGGAGATCAAG |

In certain embodiments, the anti-FGFR2b antibodies provided herein may contain one or more modifications or substitutions in one or more variable region sequences provided herein, yet retaining specific binding affinity to FGFR2b and/or FGFR 1b. In certain embodiments, at least one (or all) of the substitution(s) in the CDR sequences, FR sequences, or variable region sequences comprises a conservative substitution(s).

Various methods known in the art can be used to achieve this purpose. For example, a library of antibody variants (such as Fab or scFv variants) can be generated and expressed with phage display technology, and then screened for the binding affinity to human FGFR2b and/or FGFR1b. For another example, computer software can be used to virtually simulate the binding of the antibodies to FGFR2b and/or FGFR1b, and identify the amino acid residues on the antibodies which form the binding interface. Such residues may be either avoided in the substitution so as to prevent reduction in binding affinity, or targeted for substitution to provide for a stronger binding.

In certain embodiments, the anti-FGFR2b antibodies provided herein comprises one or more amino acid residue substitutions in one or more CDR sequences, and/or one or more FR sequences within SEQ ID NOs: 1-7. In certain embodiments, no more than 10, 9, 8, 7, 6, 5, 4, 3, 2, or 1 substitutions are made to the CDR sequences and/or FR sequences in total.

In certain embodiments, the anti-FGFR2b antibodies comprise 1, 2, 3, 4, 5, or 6 CDR sequences having at least 80% (e.g. at least 85%, 88%, 90%, 91%, 92%, 93%, 94%, 95%, 96%, 97%, 98%, or 99%) sequence identity to that (or those) listed in SEQ ID NOs: 1-7, and in the meantime retain the binding affinity to FGFR2b and/or FGFR1b at a level similar to or even higher than its parent antibody.

In certain embodiments, the anti-FGFR2b antibodies comprise one or more variable region sequences having at least 80% (e.g. at least 85%, 88%, 90%, 91%, 92%, 93%, 94%, 95%, 96%, 97%, 98%, or 99%) sequence identity to that (or those) listed in Table 2, and in the meantime retain the binding affinity to FGFR2b and/or FGFR1b at a level similar to or even higher than its parent antibody. In some embodiments, a total of 1 to 10 amino acids have been substituted, inserted, or deleted in a variable region sequence listed in Table 2. In some embodiments, the substitutions, insertions, or deletions occur in regions outside the CDRs (e.g., in the FRs).

In certain embodiments, the anti-FGFR2b antibodies provided herein comprise a constant region capable of inducing effector function such as ADCC or CDC. Effector functions such as ADCC and CDC can lead to cytotoxicity to cells expressing FGFR, and can be evaluated using various assays such as Fc receptor binding assay, C1q binding assay, and cell lysis assay. In certain embodiments, the constant region is of IgG1 isotype, which is known to induce ADCC.

In certain embodiments, the anti-FGFR2b antibodies comprise one or more modifications in the constant region that renders enhanced ADCC. As used herein, the term "enhanced ADCC" is defined as either an increase in the number of target cells that are lysed in a given time, at a given concentration of antibody in the medium surrounding the target cells, by the mechanism of ADCC defined above, and/or a reduction in the concentration of antibody, in the medium surrounding the target cells, required to achieve the lysis of a given number of target cells in a given time, by the mechanism of ADCC.

To assess ADCC activity of a molecule of interest, an in vitro ADCC assay, such as that described in U.S. Pat. No. 5,500,362; Hellstrom et al. Proc Natl Acad Sci USA 83, 7059-7063 (1986) and Hellstrom et al, Proc Natl Acad Sci USA 82, 1499-1502 (1985); U.S. Pat. No. 5,821,337; or Bruggemann et al, J Exp Med 166, 1351-1361 (1987) may be performed. Alternatively, non-radioactive assays methods may be employed (see, for example, ACTI™ non-radioactive cytotoxicity assay for flow cytometry (Cell Technology Inc., Mountain View, CA); and CytoTox 96® non-radioactive cytotoxicity assay (Promega, Madison, WI)). Additionally, ADCC activity of the molecule of interest may be assessed in vivo, e.g., in an animal model such as that disclosed in Clynes et al., PNAS (USA) 95:652-656 (1998).

Various methods for ADCC enhancement have been described in prior art. For example, it has been demonstrated that a subset of amino acid residues in the Fc region are involved in the binding to FcγRs, such as, the following amino acid residues (EU numbering of residues): (1) Lys274-Arg301 and Tyr407-Arg416 (Sarmay et al. (1984) Mol. Immunol., 21:43-51 and Gergely et al. (1984) Biochem. Soc. Tans., 12:739-743); (2) Leu234-Ser239, Asp265-Glu269, Asn297-Thr299, and Ala327-Ile332 (Sondermann et al. (2000) Nature, 406:267-273, and (3) T256, K290, S298, E333, K334, A339 (Shields et al. (2001) J. Biol. Chem., 276:6591-6604; and U.S. Patent Application No. 2004/0228856) in the Fc region are involved in the binding to human FcγRIIIA. The above-listed amino acid residues can be mutated to enhance ADCC activity, for example, in Shields et al. (2001), J Biol Chem 9(2), 6591-6604, Fc variants T256A, K290A, S298A, E333A, K334A, and A339T have been proved to enhance ADCC activity as compared to native sequences.

Alternatively, enhanced ADCC activity can be obtained by engineering the glycosylation forms of an antibody. A number of glycosylation forms have been reported to enhance ADCC activity of an antibody through enhancing its binding to the Fc receptor of the effector cells. The different glycosylation form includes any of several forms of glycans attached to the antibody, with different saccharides (e.g., lacks one type of saccharide such as fucose, or has a high level of one type of saccharide such as mannose), or having a different structure (e.g., various branched structure, such as biantennary (two branches), triantennary (three branches) or tetraantennary (four branches) structures).

In certain embodiments, the anti-FGFR2b antibodies provided herein are glyco-engineered. A "glyco-engineered" antibody or antigen-binding fragment may have an increased or decreased glycosylation level, a change in the glycosylation form, or both, as compared to its non-glyco-engineered counterpart. In certain embodiments, the glyco-engineered antibodies exhibit enhanced ADCC activity than its non-engineered counterpart. In some embodiments, the enhanced ADCC activity is characterized in at least 10%, 15%, 20%, 25%, 30%, 35%, 40%, 45%, 50%, 60%, 65%, 70%, or 75% higher lysis of FGFR2b expressing cell.

The antibodies can be glyco-engineered by methods known in the art, including any manipulation to the peptide backbone (e.g., modifications to the amino acid sequence, and/or to the side chain group of individual amino acids), and/or, manipulation to the post-translational modifications through a host cell line (e.g., modifications to glycosylation pattern). Methods of altering ADCC activity by engineering of glycosylation of an antibody have also been described in the art, see for example, Weikert et al. (1999) Nature Biotech., 17:116-121; Shields R. L. et al. (2002), J. Biol. Chem., 277:26733-26740; Shinkawa et al. (2003), J Biol Chem., 278, 3466-3473; Ferrara et al. (2006), Biotech. Bioeng., 93, 851-861; Yamane-Ohnuki et al. (2004), Biotech Bioeng., 87, 614-622; Niwa et al. (2006), J Immunol Methods 306, 151-160; Shinkawa T. et al, J. Biol. Chem, (2003), 278:3466-3473.

In some embodiments, the glyco-engineered antibodies provided herein are afucosylated (i.e. contain no fucose). Several studies have shown that afucosylated (i.e., fucose deficient, or non-fucosylated) antibody exhibited an increased binding to FcγRIII and thus provoked a higher ADCC activity (Shields et al. (2002) J. Biol. Chem., 277: 26733-26740; Shinkawa et al. (2003) J. Biol. Chem., 278: 3466-3473; and European Patent Appln. Pub. No. 1176195). In some embodiments, the afucosylated antibody provided herein lacks fucose at asparagine 297 (Asn297) of the heavy chain (based on Kabat numbering). Asn297 is a conserved N-linked glycosylation site found in each CH2 domain of the Fc region of IgG1 isotype of antibodies (Arnold et al., Glycobiology and Medicine, 564:27-43, 2005).

In some embodiments, the glyco-engineered antibodies provided herein are characterized in a high mannose glycosylation form (e.g., mannose e5, mannose 7, 8, 9 glycan). High mannose glycosylation form has been proved to enhance ADCC activity (Yu et al. (2012), Landes Bioscience, mAbs 4:4, 475-487).

In some embodiments, the antibody provided herein further comprises within its constant region one or more modifications which: a) introduces or removes a glycosylation site, b) introduces a free cysteine residue, c) enhances binding to an activating Fc receptor, and/or d) enhances ADCC.

The anti-FGFR2b antibody or antigen binding fragment thereof may comprise one or more amino acid residues with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except for proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence of the antibody is substituted. A new glycosylation site can be created in a similar way by introducing such a tripeptide sequence or serine or threonine residue.

The anti-FGFR2b antibodies provided herein also encompass a cysteine-engineered variant, which comprises one or more introduced free cysteine amino acid residues. A free cysteine residue is one which is not part of a disulfide bridge. A cysteine-engineered variant is useful for conjugation with for example, a cytotoxic and/or imaging compound, a label, or a radioisotope among others, at the site of the engineered cysteine, through for example a maleimide or haloacetyl. Methods for engineering antibodies to introduce free cysteine residues are known in the art, see, for example, WO2006/034488.

The anti-FGFR2b antibodies provided herein also encompass an Fc variant, which comprises one or more amino acid residue modifications or substitutions at its Fc region and/or hinge region. In certain embodiments, the anti-FGFR2b antibodies comprise one or more amino acid substitution(s) that improves pH-dependent binding to neonatal Fc receptor (FcRn). Such a variant can have an extended pharmacokinetic half-life, as it binds to FcRn at acidic pH which allows it to escape from degradation in the transporting lysosome and then be translocated and released out of the cell. Methods of engineering an antibody and antigen-binding fragment thereof to improve binding affinity with FcRn are well-known in the art, see, for example, Vaughn, D. et al, Structure, 6 (1):63-73 (1998); Kontermann, R. et al, Antibody Engineering, Volume 1, Chapter 27: Engineering of the Fc region for improved PK, published by Springer, 2010; Yeung, Y. et al, Cancer Research, 70:3269-3277 (2010); and Hinton, P. et al, J. Immunology, 176:346-356 (2006).

Binding Property

The anti-FGFR2b antibodies provided herein are capable of specifically binding to FGFR2b and FGFR1b. In certain embodiments, the antibodies provided herein specifically bind to human FGFR2b and/or FGFR1b with a binding affinity ($K_D$) of $\leq 10^{-6}$ M (e.g., $\leq 5\times10^{-7}$ M, $\leq 2\times10^{-7}$ M, $\leq 10^{-7}$ M, $\leq 5\times10^{-8}$ M, $\leq 2\times10^{-8}$ M, $\leq 10^{-8}$ M, $\leq 5\times10^{-9}$ M, $\leq 4\times10^{-9}$ M, $\leq 3\times10^{-9}$ M, $\leq 2\times10^{-9}$ M, $\leq 10^{-9}$ M, $\leq 9\times10^{-10}$ M, $\leq 8\times10^{-10}$ M, $\leq 7\times10^{-10}$ M, $\leq 6\times10^{-10}$ M, $\leq 5\times10^{-10}$ M, $\leq 4\times10^{-10}$ M, $\leq 3\times10^{-10}$ M, $\leq 2.5\times10^{-10}$ M, $\leq 2\times10^{-10}$ M, $\leq 1.5\times10^{-10}$ M, $\leq 10^{-10}$ M, $\leq 9\times10^{-11}$ M, $\leq 5\times10^{-11}$ M, $\leq 4\times10^{-11}$ M, $\leq 3\times10^{-11}$ M, $\leq 2\times10^{-11}$ M, or $\leq 10^{-11}$ M).

In some embodiments, the anti-FGFR2b antibodies provided herein are capable of specifically binding to human FGFR2b with a binding affinity ($K_D$) of no more than $5\times10^{-9}$ M, no more than $4\times10^{-9}$ M, no more than $3\times10^{-9}$ M, no more than $2\times10^{-9}$ M, no more than $10^{-9}$ M, no more than $5\times10^{-10}$ M, no more than $4\times10^{-10}$ M, no more than $3\times10^{-10}$ M, no more than $2\times10^{-10}$ M, no more than $10^{-10}$ M, no more than $5\times10^{-11}$ M, or no more than $4\times10^{-11}$ M, no more than $3\times10^{-11}$ M, no more than $2\times10^{-11}$ M, as measured by Biacore.

In some embodiments, the anti-FGFR2b antibodies provided herein are capable of specifically binding to human FGFR1b with a binding affinity ($K_D$) of no more than $5\times10^{-9}$ M, no more than $4\times10^{-9}$ M, no more than $3\times10^{-9}$ M, no more than $2\times10^{-9}$ M, no more than $10^{-9}$ M, no more than $5\times10^{-10}$ M, no more than $4\times10^{-10}$ M, no more than $3\times10^{-10}$ M, no more than $2\times10^{-10}$ M, no more than $10^{-10}$ M, no more than $5\times10^{-11}$ M, or no more than $4\times10^{-11}$ M, no more than $3\times10^{-11}$ M, no more than $2\times10^{-11}$ M as measured by Biacore.

In certain embodiments, the anti-FGFR2b antibodies provided herein cross-react with a Cynomolgus monkey FGFR counterpart, rat FGFR counterpart, and mouse FGFR counterpart.

Binding of the antibodies to human FGFR2b and/or FGFR1b can also be represented by "half maximal effective concentration" ($EC_{50}$) value, which refers to the concentration of an antibody where 50% of its maximal effect (e.g., binding or inhibition etc.) is observed. The $EC_{50}$ value can be measured by methods known in the art, for example, sandwich assay such as ELISA, Western Blot, flow cytometry assay, and other binding assay. In certain embodiments, the antibodies provided herein specifically bind to human FGFR2b and/or FGFR1b at an $EC_{50}$ (i.e. 50% binding concentration) of no more than 5 nM, no more than 4 nM, no more than 3 nM, no more than 2 nM, no more than 1.5 nM, no more than 1 nM, no more than 0.9 nM, no more than 0.8 nM, no more than 0.7 nM, no more than 0.6 nM, no more than 0.5 nM, no more than 0.4 nM, no more than 0.3 nM, no more than 0.2 nM or no more than 0.1 nM by ELISA. In certain embodiments, the antibodies provided herein specifically bind to human FGFR2b and/or FGFR1b at an $EC_{50}$ (i.e. 50% binding concentration) of no more than 10 nM, no more than 9 nM, no more than 8 nM, no more than 7 nM, no more than 6 nM, no more than 5 nM, no more than 4 nM, no more than 3 nM, no more than 2 nM, no more than 1 nM, no more than 0.8 nM, no more than 0.5 nM or no more than 0.3 nM by flow cytometry.

In certain embodiments, the antibodies provided herein are also capable of specifically binding to Cynomolgus monkey FGFR2b and/or FGFR1b, and/or to rat/mouse FGFR2b and/or FGFR1b. In certain embodiments, the binding affinity of antibodies provided herein to human FGFR2b and/or FGFR1b is similar to that that of rat/mouse FGFR2b and/or FGFR1b.

In certain embodiments, the antibodies provided herein have a specific binding affinity to human FGFR2b and/or FGFR1b which is sufficient to provide for diagnostic and/or therapeutic use.

In certain embodiments, the antibodies provided herein block binding of human FGFR2b and/or FGFR1b to its ligand and thereby providing biological activity including, for example, inhibition of the proliferation of FGFR2b and/or FGFR1b expressing cells.

The proliferation inhibition effect can be represented by "50% growth inhibition concentration" (GI50) value, which refers to the concentration of an antibody where 50% of its maximal proliferation inhibition effect is observed. The GI50 value can be measured by methods known in the art, for example, 3-(4,5-dimethylthiazol-2-yl)-5-(3-carboxymethoxy phenyl)-2-(4-sulfophenyl)-2H-tetrazolium (MTS) colorimetric assay (see described in U.S. Pat. No. 5,185,450), 3-(4,5-dimethytthiazol-2-yl)-2,5-diphenyltetrazolim bromide (MTT) assay (see in Berridge et. al. Biotechnol Annu Rev. 2005; 11:127-52), Alamarblue assay (see described in U.S. Pat. No. 5,501,959) and any other methods as described in Assay Guidance Manual (Sittampalam et al., editors. 2004). In certain embodiments, the antibodies provided herein are capable of inhibiting proliferation of cells having human FGFR2b expressed on their surface with a 50% Growth Inhibition concentration (GI50) of no more than 15 nM, no more than 14 nM, no more than 13 nM, no more than 12 nM, no more than 11 nM, no more than 10 nM, no more than 9 nM, no more than 8 nM, no more than 7 nM, no more than 6 nM, no more than 5 nM, no more than 2 nM, or no more than InM as measured by MTS.

Antigen-Binding Fragments

The present disclosure also provides antigen-binding fragments that can specifically bind to FGFR2b and/or FGFR1b. Various types of antigen-binding fragments are known in the art and can be developed based on the anti-FGFR2b antibodies provided herein, including for example, the exemplary antibodies whose CDR and variable sequences are shown in SEQ ID NOs: 1-7 and in Table 2, and their different variants containing modification or substitution.

In certain embodiments, an anti-FGFR2b antigen-binding fragment provided herein is a camelized single domain antibody, a diabody, a single chain Fv fragment (scFv), an scFv dimer, a BsFv, a dsFv, a $(dsFv)_2$, a dsFv-dsFv', an Fv fragment, a Fab, a Fab', a $F(ab')_2$, a bispecific antibody, a ds diabody, a nanobody, a domain antibody, a single domain antibody, or a bivalent domain antibody.

Various techniques can be used for the production of such antigen-binding fragments. Illustrative methods include, enzymatic digestion of intact antibodies (see, e.g., Morimoto et al., Journal of Biochemical and Biophysical Methods 24:107-117 (1992); and Brennan et al., Science, 229:81 (1985)), recombinant expression by host cells such as *E. Coli* (e.g. for Fab, Fv and ScFv antibody fragments), screening from a phase display library as discussed above (e.g. for ScFv), and chemical coupling of two Fab'-SH fragments to form $F(ab')_2$ fragments (Carter et al., Bio/Technology 10:163-167 (1992)). Other techniques for the production of antibody fragments will be apparent to a skilled practitioner.

In certain embodiments, the antigen-binding fragment is a scFv. Generation of scFv is described in, for example, WO 93/16185; U.S. Pat. Nos. 5,571,894; and 5,587,458. ScFv may be fused to an effector protein at either the amino or the carboxyl terminus to provide for a fusion protein (see, for example, Antibody Engineering, ed. Borrebaeck).

Conjugates

In some embodiments, the anti-FGFR2b antibodies further comprise a conjugate moiety. The conjugate moiety can be linked to an antibody provided herein. A conjugate moiety is a non-proteinaceous or peptic moiety that can be attached to the antibody. It is contemplated that a variety of conjugate moieties may be linked to the antibodies provided herein (see, for example, "Conjugate Vaccines", Contributions to Microbiology and Immunology, J. M. Cruse and R. E. Lewis, Jr. (eds.), Carger Press, New York, (1989)). The conjugate moiety may be linked to the antibody by covalent binding, affinity binding, intercalation, coordinate binding, complexation, association, blending, or addition, among other methods.

In certain embodiments, the anti-FGFR2b antibody is linked to one or more conjugates via a linker. In certain embodiments, the linker is a hydrazine linker, a disulfide linker, a bifunctional linker, dipeptide linker, glucuronide linker, or a thioether linker. In certain embodiments, the linker is a lysosomally cleavable dipeptide, e.g. valine-citrulline (vc).

The conjugate moiety can be a therapeutic agent (e.g., a cytotoxic agent), a radioactive isotope, a detectable label (e.g., a lanthanide, a luminescent label, a fluorescent label, or an enzyme-substrate label), a pharmacokinetic modifying moiety, or a purifying moiety (such as a magnetic bead or nanoparticle).

Examples of detectable label may include a fluorescent label (e.g. fluorescein, rhodamine, dansyl, phycoerythrin, or Texas Red), enzyme-substrate label (e.g. horseradish peroxidase, alkaline phosphatase, luceriferases, glucoamylase, lysozyme, saccharide oxidases or β-D-galactosidase), radioisotope, luminescent label, chromophoric moiety, digoxigenin, biotin/avidin, a DNA molecule or gold for detection.

Examples of radioisotopes may include $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}$ At, $^{186}Re$, $^{188}Re$, $^{153}Sm$, $^{212}Bi$, $^{32}P$ and other lanthanides. Radioisotope labelled antibodies are useful in receptor targeted imaging experiments.

In certain embodiments, the pharmacokinetic modifying moiety can be a clearance-modifying agent which helps increase half-life of the antibody. Illustrative examples include water-soluble polymers, such as PEG, carboxymethylcellulose, dextran, polyvinyl alcohol, polyvinyl pyrrolidone, copolymers of ethylene glycol/propylene glycol, and the like. The polymers may be of any molecular weight, and may be branched or unbranched. The number of polymers attached to the antibody may vary, and if more than one polymer are attached, they can be the same or different molecules.

In certain embodiments, the conjugate moiety can be a purification moiety such as a magnetic bead or a nanoparticle.

Antibody-Drug Conjugates

In certain embodiments, the conjugates provided herein are antibody-drug conjugates (ADC) comprising any of the above anti-FGFR2b antibodies conjugated to a cytotoxic agent. In other words, the conjugate moiety comprises a cytotoxic agent.

ADCs can be useful for local delivery of a cytotoxic agent, for example, in the treatment of cancer. This allows for targeted delivery of cytotoxic agents to tumors and intracellular accumulation therein, which is particularly useful where systemic administration of these unconjugated cytotoxic agents may result in unacceptable levels of toxicity to normal cells as well as the tumor cells sought to be eliminated (Baldwin et al., (1986), Lancet, 603-05; Thorpe, (1985), Monoclonal Antibodies, 84; Pinchera et al. (ed.s), Biological And Clinical Applications, 475-506; Syrigos and Epenetos (1999), Anticancer Research 19:605-614; Niculescu-Duvaz and Springer (1997) Adv. Drg Del. Rev. 26:151-172; and U.S. Pat. No. 4,975,278).

A "cytotoxic agent" can be any agent that is detrimental to cancer cells or that can damage or kill cancer cells. In certain embodiments, the cytotoxic agent is optionally a chemotherapeutic agent (such as a growth inhibitory agent, a DNA-alkylators, a topoisomerase inhibitor, a tubulin-binders, or other anticancer drugs), a toxin, or a highly reactive radioactive isotope.

Examples of cytotoxic agent include large molecular bacterial toxins and plant toxins, such as for example, diphtheria toxin, exotoxin A chain (from *Pseudomonas aeruginosa*), ricin, abrin, modeccin, alpha-sarcin, *Aleurites fordii*, proteins, dianthin proteins, *Phytolaca americana* proteins (PARI, PAPII, and PAP-S), *Momordica charantia* inhibitor, curcin, crotin, *Sapaonaria officinalis* inhibitor, gelonin, restrictocin, phenomycin, enomycin, and the tricothecenes (see, e.g., WO 93/21232). Such a large molecule toxin can be conjugated to the antibodies provided herein using methods known in the art, for example, as described in Vitetta et al (1987) Science, 238:1098.

The cytotoxic agent can also be small molecule toxins and chemotherapeutic drugs, such as geldanamycin (Mandler et al (2000) Jour. of the Nat. Cancer Inst. 92 (19):1573-1581; Mandler et al (2002) Bioconjugate Chem. 13:786-791), maytansinoids (EP 1391213; Liu et al., (1996) Proc. Natl. Acad. Sci. USA 93:8618-8623), calicheam icin (Lode et al (1998) Cancer Res. 58:2928; Hinman et al (1993) Cancer Res. 53:3336-3342), taxol, cytochalasin B, gramicidin D, ethidium bromide, emetine, mitomycin, etoposide, tenoposide, vincristine, vinblastine, vindesine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine), calicheamicin, maytansinoids, dolastatins, auristatins (such as monomethyl auristatin E (MMAE) and Monomethyl auristatin F (MMAF)), a trichothecene, and CC1065, and the derivatives thereof having cytotoxic activity. Such toxin can be conjugated to the antibodies provided herein using methods known in the art, for example, as described in U.S. Pat. No. 7,964,566; Kline, T. et al, Pharmaceutical Research, 32 (11):3480-3493.

The cytotoxic agent can also be a highly radioactive isotope. Examples include $At^{211}$, $I^{131}$, $I^{125}$, $Y^{90}$, $Re^{186}$, $Sm^{153}$, $Bi^{212}$, $p^{32}$, $Pb^{212}$ and radioactive isotopes of Lu. Methods of conjugation of a radioisotope to an antibody is known in the art, for example, via a suitable ligand reagent (see, e.g., WO94/11026; Current Protocols in Immunology, Volumes 1 and 2, Coligen et al, Ed. Wiley-Interscience, New York, N.Y., Pubs. (1991)). A ligand reagent has a chelating ligand that can bind, chelate or otherwise complex a radioisotope metal, and also has a functional group that is reactive with a thiol of cysteine of an antibody or antigen-binding fragment. Exemplary chelating ligands include DOTA, DOTP, DOTMA, DTPA and TETA (Macrocyclics, Dallas, Tex.).

In certain embodiments, the antibodies are attached to the conjugate moiety via a linker, for example, a hydrazine linker, a disulfide linker, a bifunctional linker, dipeptide linker, glucuronide linker, or a thioether linker.

Exemplary bifunctional linkers include, such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluom-2,4-dinitrobenzene).

In certain embodiments, the linker is cleavable under a particular physiological environment, thereby facilitating release of the cytotoxic agent in the cell. For example, the linker can be an acid-labile linker, peptidase-sensitive linker, photolabile linker, dimethyl linker or disulfide-containing linker (Chari et al., Cancer Research 52:127-131 (1992); U.S. Pat. No. 5,208,020). In some embodiments, the linker may comprise amino acid residues, such as a dipeptide, a tripeptide, a tetrapeptide or a pentapeptide. The amino acid residues in the linker may be natural or non-naturally occurring amino acid residues. Examples of such linkers include: valine-citrulline (ve or val-cit), alanine-phenylalanine (af or ala-phe), glycine-valine-citrulline (gly-yal-cit), glycine-glycine-glycine (gly-gly-gly), an valine-citrullin-p-aminobenzyloxycaronyl ("vc-PAB"). Amino acid linker components can be designed and optimized in their selectivity for enzymatic cleavage by a particular enzyme, for example, a tumor-associated protease, cathepsin B, C and D, or a plasmin protease.

In certain embodiments, in the ADC provided herein, an antibody (or antigen-binding fragment) is conjugated to one or more cytotoxic agents at an antibody: agent ratio of about 1 to about 20, about 1 to about 6, about 1 to about 3, about 1 to about 2, about 1 to about 1, about 2 to about 5, or about 3 to about 4.

The ADC provided herein may be prepared by any suitable methods known in the art. In certain embodiments, a nucleophilic group of the antibody is first reacted with a bifunctional linker reagent and then linked to the cytotoxic agent, or the other way around, i.e., first reacting a nucleophilic of the cytotoxic agent with a bifunctional linker and then linking to the antibody.

In certain embodiments, the cytotoxic agent may contain (or modified to contain) a thiol reactive functional group which may react with a cysteine thiol of a free cysteine of the antibodies provided herein. Exemplary thiol-reactive functional group include, for example, a maleimide, an iodoacetamide, a pyridyl disulfide, haloacetyl, succinimidyl ester (e.g., NHS, N-hydroxysuccinimide), isothiocyanate, sulfonyl chloride, 2,6-dichlorotriazinyl, pentafluorophenyl ester, or phosphoramidite (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671).

The cytotoxic agent or the antibody may react with a linking reagent before being conjugated to form the ADC. For example, N-hydroxysuccinimidyl ester (NHS) of a cytotoxic agent may be performed, isolated, purified, and/or characterized, or it may be formed in situ and reacted with a nucleophilic group of an antibody.

In some embodiments, the cytotoxic agent and the antibody may be linked by in situ activation and reaction to form the ADC in one step. In another example, the antibody may be conjugated to biotin, then indirectly conjugated to a second conjugate that is conjugated to avidin.

In certain embodiments, the conjugate moiety is randomly attached to a specific type of surface-exposed amino acid residue in the antibody, for example a cysteine residue or a lysine residue.

In certain embodiments, the conjugate moiety is attached to a specifically defined site to provide ADC populations with high homogeneity and batch-to-batch consistency with respect to drug-to-antibody ratio (DAR) and attachment site. In certain embodiments, the conjugate moiety is attached to specifically defined sites in antibody molecules via natural amino acids, unnatural amino acid, short peptide tags, or Asn297 glycans. For example, the conjugation may be at a specific site outside the epitope binding portion.

Site-specific attachment can be achieved by substituting a native amino acid at a specific site of the antibody with, or introducing before/after a specific site of the antibody, an amino acid such as cysteine to which a drug moiety can be conjugated (see Stimmel et al. (2000), JBC, 275 (39):30445-30450; Junutula et al. (2008), Nature Biotechnology, 26 (8):925-932; and WO2006/065533). Alternatively, site-specific conjugation can be achieved by engineering antibodies to contain unnatural amino acids (e.g., p-acetylphenylalanine (pAcF), N6-((2-azidoethoxy) carbonyl)-L-lysine, p-azidomethyl-L-phenylalanine (pAMF), and selenocysteine (Sec)) at specific sites in their heavy and/or light chains as described by Axup et al. ((2012), Proc Natl Acad Sci USA. 109 (40):16101-16116), wherein the unnatural amino acids provide the additional advantage that orthogonal chemistry can be designed to attach the linker reagent and drug. Exemplary specific sites (e.g., light chain V205, heavy chain A114, S239, H274, Q295, S396, etc.) useful in the two above-described site-specific conjugation method are described in many prior arts, for example, Strop et al. (2013), Chemistry & Biology, 20, 161-167; Qun Zhou (2017), Biomedicines, 5, 64; Dimasi et al. (2017), Mol. Pharm., 14, 1501-1516; WO2013/093809 and WO2011/005481. Another site-specific ADC conjugation method is glycan-mediated conjugation, in which a drug-linker can be conjugated to Asn297 glycans (such as fucose, galactose, N-acetylgalactosamine, N-acetylglucosamine, sialic acid) located in CH2 domain instead of coupling the relatively hydrophobic cytotoxic agent into amino acid backbone of the antibody. Efforts have also been made to introduce unique short peptide tags (such as LLQG, LPETG, LCxPxR) into antibodies via specific sites (e.g., sites in N terminal or C terminal regions), which then allow specific amino acids in the peptide tags to be functionalized and coupled to the drug-linkers (Strop et al. (2013), Chemistry & Biology, 20, 161-167; Beerli et al. (2015), PLOS ONE, 10, e0131177; Wu et al. (2009), Proc. Natl. Acad. Sci. 106, 3000-3005; Rabuka (2012), Nat. Protoc. 7, 1052-1067).

Polynucleotides and Recombinant Methods

The present disclosure provides isolated polynucleotides that encode the anti-FGFR2b antibodies provided herein.

The term "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

In certain embodiments, the isolated polynucleotides comprise one or more nucleotide sequences as shown in SEQ ID NO: 9, 11, 13, 15, 17, and/or a homologous sequence thereof having at least 80% (e.g. at least 85%, 88%, 90%, 92%, 93%, 94%, 95%, 96%, 97%, 98%, or 99%) sequence identity, and/or a variant thereof having only degenerate substitutions, and encodes the variable region of the exemplary antibodies provided herein. DNA encoding the monoclonal antibody is readily isolated and sequenced using conventional procedures (e.g., by using oligonucleotide probes that are capable of binding specifically to genes encoding the heavy and light chains of the antibody). The encoding DNA may also be obtained by synthetic methods.

The isolated polynucleotide that encodes the anti-FGFR2b antibodies (e.g. including the sequences as shown in Table 3) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence. A vector may also include materials to aid in its entry into the cell, including but not limited to a viral particle, a liposome, or a protein coating.

The present disclosure provides vectors (e.g., cloning vectors or expression vectors) containing the nucleic acid sequence provided herein encoding the antibodies, at least one promoter (e.g., SV40, CMV, EF-1a) operably linked to the nucleic acid sequence, and at least one selection marker. Examples of vectors include, but are not limited to, plasmids, phagemids, cosmids, and artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as expression vectors include retrovirus (including lentivirus), adenovirus, adeno-associated virus, herpesvirus (e.g., herpes simplex virus), poxvirus, baculovirus, papillomavirus, and papovavirus (e.g., SV40). Exemplary plasmids include, pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT.RTM., pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces.*

In addition to prokaryotes, eukaryotic microbes such as filamentous fungi or yeast are suitable cloning or expression hosts for anti-FGFR2b antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), K. *bulgaricus* (ATCC 16,045), K. wickeramii (ATCC 24,178), *K. waltii* (ATCC 56,500), K. *drosophilarum* (ATCC 36,906), *K. thermotolerans*, and *K. marxianus; yarrowia* (EP 402,226); *Pichia pastoris* (EP 183,070); *Candida, Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse myeloma cell line (NSO, Galfrè and Milstein (1981), Methods in Enzymology, 73:3-46; Sp2/0-Ag14, ATCC CRL-1581); Chinese hamster ovary cells/-DHFR (CHO, Urlaub et al., *Proc. Natl. Acad. Sci. USA* 77:4216 (1980)); mouse sertoli cells (TM4, *Mather, Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). In some preferable embodiments, the host cell is mammalian cultured cells, such as CHO cells, BHK cells, or NSO cells.

In some embodiments, the host cell is capable of producing a glyco-engineered antibody. For example, a host cell line can provide for the required glycosylation machinery during post-translation modification. Examples of such host cell lines includes but are not limited to those with altered (increased or decreased) activity of glycosylation related enzymes, such as, glucosaminyltransferase (e.g., β (1,4)-N-acetylglucosaminyltransferase III (GnTIII)), glycosyltransferase (e.g., β (1,4)-galactosyltransferase (GT)), sialyltransferase (e.g., α(2,3)-sialyltransferase (ST)), mannosidase (e.g., α-mannosidase II (ManII), fucosyltransferase (e.g., alpha-1,6-fucosyltransferase gene (FUT8), (1,3) fucosyltransferase), prokaryotic GDP-6-deoxy-D-lyxo-4-hexulose reductase (RMD), GDP-fucose transporter (GFT), natively or through genetic engineering.

In some embodiments, the host cell is characterized in lack of functional FUT8, overexpression of a heterologous GnTIII, expression of a prokaryotic GDP-6-deoxy-D-lyxo-4-hexulose reductase (RMD), or lack of functional GFT. A FUT8 knock out host cell line is fucosylation-deficient and produces afucosylated antibodies. Overexpression of GnTIII in a host cell line (see for example, the Glycart technology by Roche) results in the formation of bisected, non-fucosylated glycosylation form of an antibody. Expression of RMD (e.g. as in GlymaxX® system from ProBioGen AG) inhibits fucose de-novo biosynthesis, and as a consequence, antibodies generated by such host cell lines also exhibit reduced fucosylation. GFT knockout in CHO cell line (see for example, technology by Beijing Mabworks Biotech) block both fucose de-novo and fucose salvage biosynthesis pathways and results in reduced fucosylation.

Host cells are transformed with the above-described expression or cloning vectors for anti-FGFR2b antibody production and cultured in conventional nutrient media modified as appropriate for inducing promoters, selecting transformants, or amplifying the genes encoding the desired sequences. In another embodiment, the antibody may be produced by homologous recombination known in the art.

The host cells used to produce the antibodies provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli.* Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-FGFR2b antibodies prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., *J. Immunol. Meth.* 62:1-13 (1983)). Protein G is recommended for all mouse isotypes and for human gamma3 (Guss et al., *EMBO J.* 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Composition

The present disclosure further provides pharmaceutical compositions comprising an anti-FGFR2b antibody provided herein and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-FGFR2b antibody or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Methods of Use

The present disclosure also provides therapeutic methods comprising: administering a therapeutically effective amount of the antibody or antigen-binding fragment as provided herein to a subject in need thereof, thereby treating or preventing a FGFR2b- and/or FGFR1b-related condition or disorder. In some embodiments, the FGFR2b- and/or FGFR1b-related condition or disorder is cancer, optionally the cancer is characterized in expressing or over-expressing FGFR2b and/or FGFR1b.

Examples of cancer include but are not limited to, ovarian cancer, endometrial cancer, breast cancer, lung cancer (small cell or non-small cell), colon cancer, prostate cancer, cervical cancer, colorectal cancer, pancreatic cancer, gastric cancer, esophageal cancer, hepatocellular carcinoma (liver cancer), renal cell carcinoma (kidney cancer), head-and-neck cancer, mesothelioma, melanoma, sarcomas, brain tumors (e.g., gliomas, such as glioblastomas), and hematological malignancies.

In some embodiments, the FGFR2b- and/or FGFR 1b-related condition or disorder is a cancer characterized in expressing or over-expressing FGFR2b and/or FGFR1b.

FGFR2b and/or FGFR1b expression or over-expression may be determined in a diagnostic or prognostic assay by evaluating increased levels of FGFRs in a biological sample (such as a sample derived from cancer cell or tissue, or tumor infiltrating immune cells) from a subject. Various methods can be used. For example, diagnostic or prognostic assay can be used to evaluate expression levels of FGFR2b and/or FGFR1b present on the surface of a cell (e.g. via an immunohistochemistry assay; IHC). Alternatively, or additionally, one may measure levels of FGFR-encoding nucleic acid in the cell, e.g. via fluorescent in situ hybridization (FISH; see WO98/45479 published October 1998), southern blotting, or polymerase chain reaction (PCR) techniques, such as real time quantitative PCR (RT-PCR). Methods 132:73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, the antibody or antigen-binding fragment as provided herein may be administered at a therapeutically effective dosage of about 0.01 mg/kg to about 100 mg/kg. In certain of these embodiments, the antibody or antigen-binding fragment is administered at a dosage of about 50 mg/kg or less, and in certain of these embodiments the dosage is 10 mg/kg or less, 5 mg/kg or less, 3 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In some embodiments, the antibodies disclosed herein may be administered alone or in combination with one or more additional therapeutic means or agents. For example, the antibodies disclosed herein may be administered in combination with another therapeutic agent, for example, a chemotherapeutic agent or an anti-cancer drug.

In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The present disclosure further provides methods of using the anti-FGFR2b antibodies.

In some embodiments, the present disclosure provides methods of detecting presence or amount of FGFR2b and/or FGFR1b in a sample, comprising contacting the sample with the antibody, and determining the presence or the amount of FGFR2b and/or FGFR1b in the sample.

In some embodiments, the present disclosure provides methods of diagnosing a FGFR2b- and/or FGFR1b-related disease or condition in a subject, comprising: a) contacting a sample obtained from the subject with the antibody provided herein; b) determining presence or amount of FGFR2b and/or FGFR1b in the sample; c) correlating the presence or the amount of FGFR2b and/or FGFR1b to existence or status of the FGFR2b- and/or FGFR1b-related disease or condition in the subject.

In some embodiments, the present disclosure provides methods of prognosing a FGFR2b- and/or FGFR1b-related disease or condition in a subject, comprising: a) contacting a sample obtained from the subject with the antibody provided herein; b) determining presence or amount of FGFR2b and/or FGFR1b in the sample; c) correlating the presence or the amount of FGFR2b and/or FGFR1b to potential responsiveness of the subject to a FGFR2b and/or a FGFR1b antagonist.

In some embodiments, the present disclosure provides kits comprising the antibody provided herein, optionally conjugated with a detectable moiety. The kits may be useful in detection of FGFR2b and/or FGFR1b or diagnosis of FGFR2b- and/or FGFR1b-related disease.

In some embodiments, the present disclosure also provides use of the antibody provided herein in the manufacture of a medicament for treating a disease or condition that would benefit from modulation of FGFR2b and/or FGFR1b expression in a subject, in the manufacture of a diagnostic/prognostic reagent for diagnosing/prognosing a FGFR2b- and/or FGFR1b-related disease or condition.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1. Cells and Reagents

Human gastric cancer cell line KATO III and SNU16 with FGFR2b expression, and Ba/F3 cells (pre-B lymphocytes) were purchased from the American Type Culture Collection (ATCC). Human esophageal cancer cell line KYSE180 was a gift from Peking University. The above-described human cell lines were cultured according to the suppliers' recommendations. Human tumor tissue was obtained from Zhongshan hospital (China) with patient's consent complying with regulations and was used to develop human lung cancer patient-derived xenograft model LC038.

To establish cell-based assays for antibody screening during antibody generation period, Ba/F3 cells were engineered to express FGFR2b or FGFR2c. The Ba/F3 cells were transfected with plasmids encoding 2b or 2c isoforms of human FGFR2. Following selection with G418, single clone with high expression of FGFR2b or FGFR2c was isolated.

The beta-isoform (IgD2 and IgD3 domains) of human FGFR2b was expressed as immunoadhesion molecules by fusing the Extra Cellular Domain ("ECD domain") residues 65-267 of FGFR2b (Genbank accession number NP_001138391) to the human Fc region (residues 100-330) in the DNA plasmids. The protein was expressed by transfecting human 293F cells (Invitrogen) and purified from culture medium using a protein A/G column.

The cDNA of Cynomolgus monkey (cyno) FGFR2b ECD domain was cloned by standard techniques from cyno skin mRNA, and amino acids 1-253 were fused to murine Fc to create cyno FGFR2b-Fc for expression. The ECD domain residues of human (hu) FGFR2b (65-267 of NP_001138391) or rat FGFR2b (56-308 of NP_001103363.1) fused with murine Fc were also expressed. The rat and mouse FGFR2b ECD are identical.

Human Fc fusion proteins of the other human FGFRs family members were all purchased from R&D Systems, including recombinant FGFR1b-Fc, FGFRIc-Fc, FGFR2c, FGFR1c-Fc, FGFR3b-Fc, FGFR3c-Fc and FGFR4-Fc protein. Alpha-isoform of FGFR2b-Fc, FGFs were also purchased from R&D Systems. Heparin was obtained from Sigma-Aldrich (SIGMA, #H3149-500KU-9). PBMC was purchased from AllCell (#LP180322).

A clinical stage anti-human FGFR2b specific antibody FPA144 was expressed according to the related patent application WO 2015/017600 A1.

Example 2. Generation of Anti-FGFRs Monoclonal Ab

Balb/c mice or SJL mice were immunized with human FGFR2b (beta)-Fc in CFA/IFA i.p. at an initial dose of 50 μg/mice then 25 μg/mice or initial dose of 10 μg/mice then 5 μg/mice. The serum titer against human FGFR2b-Fc or human FGFR2c-Fc was determined by ELISA. Four days after the final injection, popliteal lymphoid cells were extracted and fused with mouse myeloma cells. Ten days after the fusion, hybridoma culture supernatants were screened first for FGFR2b (beta)-Fc vs NC-Fc (Fc fragments as negative control) binding by the ELISA. Hybridomas with antibodies that bind to FGFR2b (beta)-Fc but do not bind to NC-Fc were selected. Hybridomas pass primary screening were subjected to secondary screening panel, including binding to BaF3/FGFR-2b cells and BaF3/FGFR-2c by FACS, blockade of FGFs ligand binding, and cell killing. Several positive clones were selected in this way, including a clone named Ab 21. The isotype of the monoclonal antibodies produced by these selected clones was determined using isotype-specific antibodies.

Example 3. Humanization of Ab 21

The heavy and light chain variable ($V_H$, $V_L$) regions sequences of the Ab 21 was determined using standard RACE technology. Total RNA were extracted from the selected hybridoma cell line. Then full-length first strand cDNA containing 5' ends was generated using SMART RACE cDNA Amplification Kit (Clontech, Palo Alto, CA) or GeneRacer kit (Invitrogen) according to manufacturer's instructions, and amplified by PCR. PCR products were isolated and purified, and then TA cloned and sequenced.

Then chimeric antibody Ab 21c was generated by grafting the $V_H$ and $V_L$ of mouse Ab 21 into a human Fc. And humanization of Ab 21 was designed, constructed and expressed using standard methods of molecular biology. In brief, the CDRs of mouse Ab 21 was grafted into a human acceptor framework. Then at framework position where the computer model suggests significant contact with CDRs, the amino acid residues from mouse antibody were substituted for human framework amino acid residues, including M69L, A93T and R94S of the heavy chain and no substitution in the light chain, using Kabat numbering. This provided for the humanized antibody of Ab 21, designated as Ab hu21-21. The amino acids Asn-Gly (NG) in the CDR2 of the heavy chain of Ab hu21-21 was further substituted with the amino acids Asn-Arg (NR), providing a variant designated as Ab hu21-26. The heavy chain or and light chain of CDRs region sequences and variable region sequences of Ab21, Ab 21c, Ab hu21-21, and Ab hu21-26 are shown in the Tables 1-3 described above.

Amino acid sequences of the entire mature Ab hu21-26 light chain and heavy chain with human IgG1 are shown in FIG. 1.

Example 4. Afucosylation of the Ab Hu21-26 and Glycan Analysis

To generate afucosylated version of Ab hu21-26 (designated as "afhu21-26" where the pre-fix "af" is short for "afucosylated"), the 1,6-fucosyltransferase knockout (FUT8−/−) CHOK1 cells (Wuxi Biologics, China, Shanghai) were used as the host cell line to produce fucose-free antibodies (i.e. afucosylated antibodies). The expression vector containing the nucleotide sequences encoding the heavy chain (HC) and light Chain (LC) of Ab hu21-26 monoclonal antibody with human IgG1 constant Fc were transiently transfected into FUT8−/− CHOK1 to produce the afucosylated antibody.

Afhu21-26 was purified by Protein A and SEC-HPLC and dialyzed to exchange into formulation buffer and stored at −80° C.

Glycan analysis of the produced afhu21-26 was performed using LC-MS. In brief, 10 μg antibody in 10 μL was digested with 1 μL of 12 units/μL IdeS enzyme (Genovis AB) for 1 hr at 37° C., followed by sequentially adding 37.5 μL of 8 M guanidine hydrochloride, 2.5 μL 1 M Tris-HCl, and 1 μL 1 M DTT, then mixing and incubating for 30 min at 10~30° C. The fully reduced antibody was separated by reverse phase-HPLC method. Then glycan profile was analyzed using LS-MS. The mass of each peak was determined and used to identify each glycan, and results were shown in the Table 4 below.

TABLE 4

Mass of glycan peaks

| Glycan | Theoretical Mass (Da) | Measured Mass(Da) |
|---|---|---|
| G0-GN | 24854.91 | 24856.57 |
| Man5 | 24976 | 24977.37 |
| G0 | 25058.11 | 25059.43 |
| G1 | 25220.25 | 25221.32 |

The results demonstrated that GOF, GIF, G2F were not detectable and antibody were almost 100% afucosylated as shown in Table 5.

TABLE 5

Glycan profile of afhu21-26
Glycan profile of afhu21-26

| G0-GN | Man5 | G0 | G1 |
|---|---|---|---|
| 1.9% | 1.9% | 85.8% | 10.4% |

Example 5. Binding Characteristics of the Antibodies

The binding of antibodies to human FGFR2b or human FGFR1b antigen was determined by surface plasmon resonance (Biacore). Briefly, CM5 sensor chip (GE Healthcare Life Sciences) was firstly activated by a 4 min injection of 1:1 freshly mixture of 50 mM N-hydroxysuccinamide (NHS):200 mM ECD domain. Then hFGFR2b-Fc or hFGFR1b-Fc was immobilized to activated CM5 sensor chip using Amine Coupling Kit (GE Healthcare Life Sciences) and 1M ethanolamine as the blocking reagent. About 20-30 response units (RU, 1 RU represents the binding of 1 μg of protein per square mm) of antigen protein were captured.

Antibodies were diluted in HBS-EP+running buffer (GE Healthcare Life Sciences) (10 mM HEPES, 150 mM NaCl, 3 mM EDTA, 0.05% surfactant P20, pH 7.4) and injected at serial concentration (0, 6.25, 12.5, 25, 50, 100, 150, 200 nM) and surface regeneration of the CM5 sensor chip were included in each running cycle. The association constant, dissociation constant were calculated with Biacore T200 evaluation software (version 1.0). As shown in FIG. 2, Ab 21c (chimeric) and its humanized variants Ab hu21-21 and Ab hu21-26 exhibited strong binding affinity to human FGFR2b, with a KD value in a range of 220~489 μM, which is better than the antibody FPA144 used as a positive control. In addition, Ab 21c is distinguished from the antibody FPA144 in terms of FGFR1b binding. Ab 21c binds to human FGFR1b potently with a KD value of 3.69 nM, comparing to very weak binding of the antibody FPA144 to human FGFR 1b with a KD value of 225 nM. Similar to Ab 21c, both Ab hu21-21 and Ab hu21-26 also exhibited specific binding to human FGFR1b (data not shown).

To confirm that the selected antibodies can bind to the endogenous forms of FGFR2b on the cell membrane, flow cytometry was performed using FGFR2b expressing KATOIII cells. All antibodies were prepared in PBS buffer with 10% donkey serum (Jackson Immunogen #017-000-121). 500,000 KATOIII cells were incubated with 100 μl of different concentration of anti-FGFR2b antibody for 60 min at 4° C. Cells were washed twice and incubated in 100 μl of 10 μg/ml of 2nd IgG-Alexa488 antibody (Jackson Immunogen #709546149) for 30 minutes at 4° C. in the dark. Cells were washed three times and resuspended with wash buffer and analyzed on a flow cytometer. The FACS data clearly showed that Ab 21c binds potently to KATOIII cells with a $EC_{50}$ value of around 8 nM, as indicated in FIG. 3. Similar to Ab 21c, both Ab hu21-21 and Ab hu21-26 also exhibited specific binding to KATOIII cells (data not shown).

Figure 4:
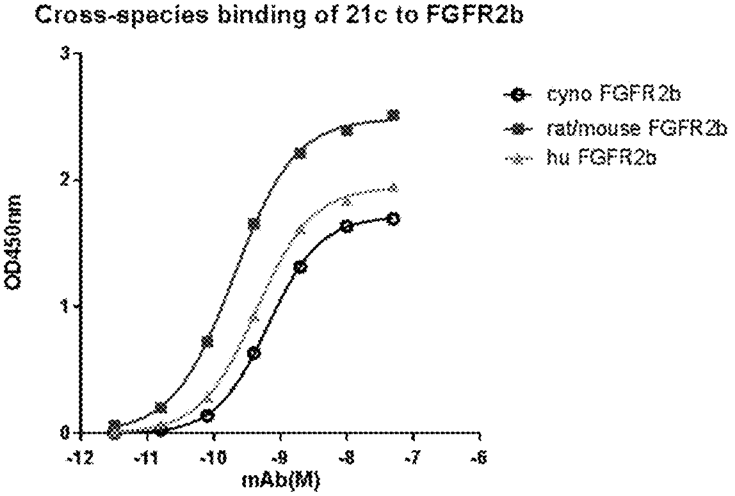
FIG. 4. Cross-species binding of the Ab 21c to human, cynomolgus, and rat/mouse FGFR2b.

The cross-species binding of Ab 21c to recombinant cyno, rat/mouse, and human FGFR2b-Fc fusion proteins was conducted with ELISA. In brief, 96-well ELISA plate were coated with about 100 μl/well 0.1 μg/ml recombinant human FGFR2b-Fc, recombinant rat/mouse FGFR2b-Fc, or recombinant cyno FGFR2b-Fc protein in PBS overnight. Then the plate was blocked with 2% BSA in PBS with 0.05% Tween20 and incubation with antibody samples for 60 min at room temperature, and then washed twice in 1×TBST (Cell Signaling Technology, #9997) and followed by incubation with anti-human lgG HRP (Horseradish peroxidase) conjugate for 60 min at a room temperature. HRP activity was detected with tetra-methylbenzidine substrate (Cell Signaling Technology, #7004) and the reaction was stopped with stop solution (Cell Signaling Technology, #7002). The plate was read at 450 nm. As shown in FIG. 4, there is no significant difference in binding $EC_{50}$ for Ab 21c to FGFR2b of different species. Ab 21c has the highest binding affinity to rat/mouse FGFR2b, followed by human FGFR2b, and then cyno FGFR2b. Similar to Ab 21c, both Ab hu21-21 and Ab hu21-26 also exhibited specific binding to FGFR2b of different species (data not shown).

Figure 5:
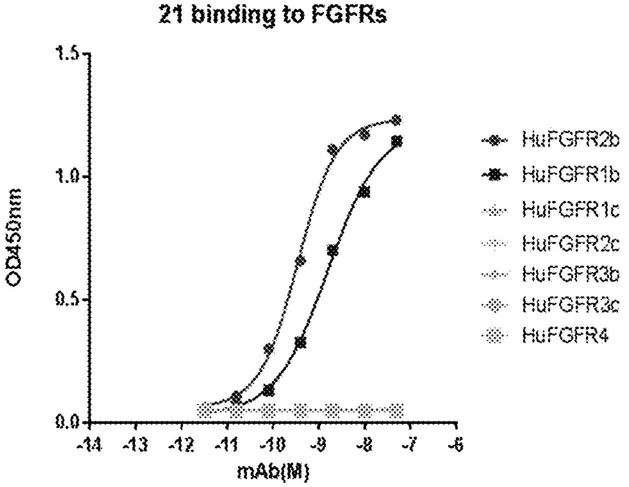
FIG. 5. Binding selectivity of the mouse Ab 21 (denoted as "21" in the figures) to various family members of human FGFRs.

Similarly, the binding specificity of Ab 21 with various FGFR family member, FGFR1b, FGFR3c, FGFR3b, FGFR4 was characterized with ELISA assay. The data is shown in FIG. 5. According to the result of ELISA analysis, Ab 21 specifically binds to FGFR2b and FGFR1b, this is consistent to the data shown in FIG. 2, and it does not bind to any other FGFR family members. Similar to Ab 21c, both Ab hu21-21 and Ab hu21-26 also exhibited specific binding to FGFR2b and FGFR1b but not to any other FGFR family members in ELISA analysis (data not shown).

Example 6. In Vitro Inhibition Activity

Figure 6:
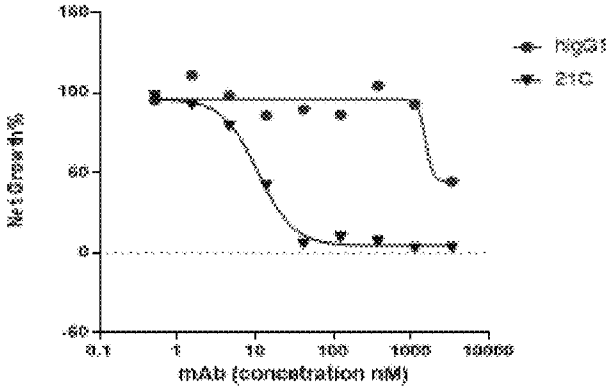
FIG. 6. Inhibition of FGF7-induced cell proliferation of Ba/F3 cells stably transfected with human FGFR2b by the Ab 21c with isotype human IgG1 as negative control.

The inhibition activity of antibody on ligand-induced cell proliferation was done in FGFR2b engineered Ba/F3 cell clones (Ba/F3-FGFR2b). Cells were seeded in 96-well plates at 30,000 cell/well in RPMI1640 medium containing 10% fetal bovine serum and Recombinant Human FGF7 Protein (10 ng/mL) in the presence of heparin (10 μg/ml). After overnight incubation, anti-FGFR2b antibody at different concentration was added to the assay plates and incubated for a further 72 hours. Following 72 hours incubation, 20 μl of CellTiter Aqueous One Solution Reagent was added to each well and the plates were incubated at room temperature for 2 hours. To measure the absorbance, 25 μl of 10% SDS was added to each well to stop the reaction. Absorbance was measured at 490 nm and 650 nm (reference wavelength) on the Tecan Spark 20M. Ab 21c can potently inhibit FGF7-induced BaF3 cell proliferation with GI50 of about 10 nM. This inhibition activity data of Ab 21cwas processed using Prism and the graph was shown in FIG. 6. Similar to Ab 21c, both Ab hu21-21 and Ab hu21-26 also exhibited potent inhibition of FGF7-induced BaF3 cell proliferation (data not shown).

Figure 7:
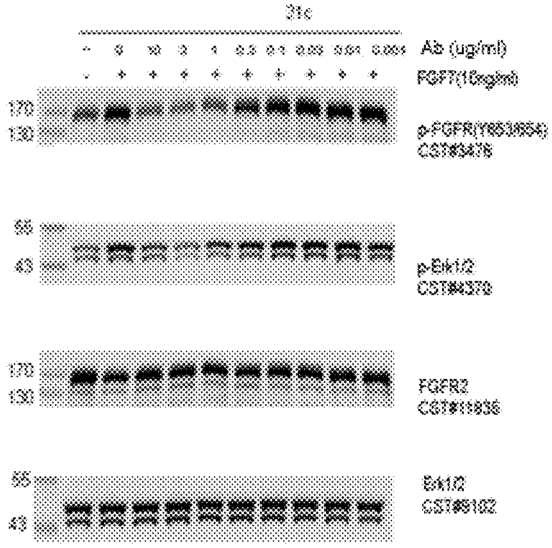
FIG. 7. The dose-dependent down-regulation of FGFR2b phosphorylation and its downstream target ERK phosphorylation by the Ab 21c.

The inhibition of FGFR2 signaling pathway by the antibody was investigated. SNU16 cells were grown in RPMI medium with 10% FBS and then seed in 30,000/well and starve in serum-free RPMI/0.1% BSA overnight. Then Cells were collected by scraping and washed once in cold PBS and then lysed in 2× SDS lysis buffer (100 mM Tris pH 6.8, 4% SDS, 20% Glycerol and 1×Protease and Phosphatase inhibitors (Pierce)). Then the lysates were boiled for 10 min at 100° C. The protein concentration was detected by the BCA protein assay kit (Pierce) and equal amount of proteins were loaded into SDS-PAGE gel then proteins were transferred to nitrocellulose membranes using iBolt (Invitrogen), which was then subjected to Western blotting analysis on phosphorylation of FGFR2 and its downstream gene ERK. As shown in FIG. 7, Ab 21c treatment results in down-regulation of phosphorylated FGFR2 and phosphorylated ERK in a dose-dependent manner on SNU16 cells. Similar to Ab 21c, both Ab hu21-21 and Ab hu21-26 also exhibited down-regulation of phosphorylated FGFR2 and phosphorylated ERK (data not shown).

Figure 8:
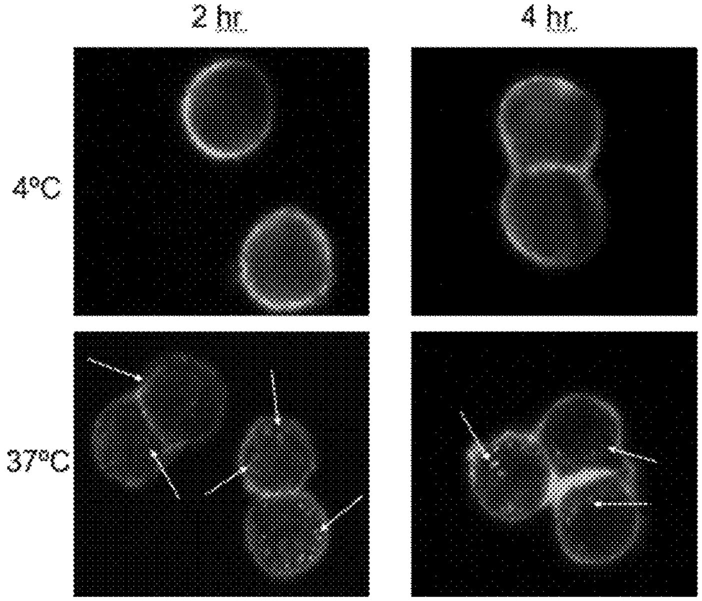
FIG. 8. Antibody internalization indicated by the confocal image of the intracellular distribution of the mouse Ab 21 after incubation with KATOIII cells at 37° C. for 2 hour and 4 hour. Confocal images of the intracellular distribution of mouse Ab 21 after incubation with KATOIII cells at 4° C. for 2 hour and 4 hour were used as a negative baseline control.

The internalization of antibody was detected by confocal microscopy. In brief, on the day of confocal microscopy, cells were collected using enzyme free dissociation solution and prepared at a density of $5\times10^5$ cells for each tube. The cells were washed and re-suspended with 100 μl blocking buffer (10% donkey serum) for 30 min at 4° C. Then cells were washed twice and incubated with 100 μl of 10 μg/ml of Ab 21 at 4° C. for 60 min. The cells were washed and split into multiple aliquots in vials, of which some were kept at 4° C., and some others at 37° C. At an indicated time point, one vial was taken from 4° C. and one vial was taken from 37° C. After washing and resuspension, cells were fixed and then blocked with 100 μl of 10% donkey serum, before washing and incubation with 10 μg/ml of donkey anti-human IgG-Alexa488 at 4° C. for 30 minutes in the dark. Cells were washed and re-suspended, and 5 μl of the cell suspension was spread on glass slide (aim to get single layer cell), dried up on 55° C. hot surface and treated with 5 μl of 1×DAPI before sealing with glass coverslip. Then confocal image was taken. As shown in FIG. 8, at 4° C. where internalization cannot happen, Ab 21 is only observed on the cell surface. After subject to 37° C. condition for 2 hr or 4 hr which allowed internalization, antibody was found intracellularly (marked by arrow), suggesting the occurrence of antibody internalization. Similar to Ab 21, all of Ab 21c, Ab hu21-21 and Ab hu21-26 also induced antibody internalization in the cells (data not shown).

Figure 9:
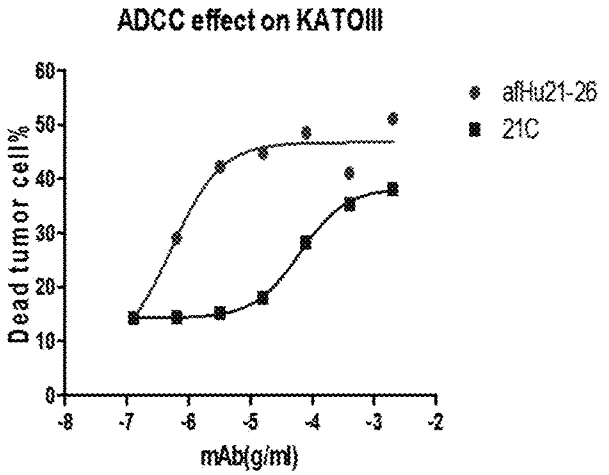
FIG. 9. ADCC activity of afucosylated Ab hu21-26 (denoted as "afhu21-26" in figures) and fucosylated antibody Ab 21c against KATOIII cells.

In vitro assays to determine the ADCC activity of antibody was performed. The ADCC assay was performed using primary NK cells isolated from human PBMCs (AllCells, CAT #PB0004F) by EasySep™ Human NK Cell Isolation Kit (Stemcell, #17955) as effector cells at an effector to target (E/T) cell ratio of 8:1. Human PBMCs were thawed in RPMI1640 containing 10% FBS+HEPES 10 mM+sodium pyruvate 1 mM the day before running the FACS assay. The target cells KATOIII were stained with cell marker CFSE-FITC (Invitrogen, #C34554) for 30 minutes and then were incubated for 5 hours at 37° C. in the presence of effectors and antibody. Then cells were stained with viability marker Viability stain-APC-Cy7 (BD, #565388). Cytotoxicity lysis was determined by FACS by gating cells positive for both CFSE staining and viability marker staining. Data was shown in FIG. 9. Afhu21-26 showed a significantly better ADCC activity as compared to Ab 21c, indicating that afucosylation improved ADCC activity of Ab 21c in both maximum lysis percentage and $EC_{50}$. Similar results are also obtained for afhu21-21 as well.

Example 7. In Vivo Antitumor Activity of Antibody in Tumor Mice Models

Immunodeficient nude mice were purchased from VitaRiver. All the animal studies were approved by IACUC, and conducted in compliance with internal and local regulatory requirements.

The SNU16 human gastric cancer Cell Line-Derived Xenograft (CDX) mice models were established by first culturing the cells in vitro, and then inoculating the cells subcutaneously into the dorsal flanks of mice at $1\times10^7$ cells/200 μl mixed with 50% Matrigel/mouse when the xenograft tumors reached the size of 300-500 $mm^3$, they were excised, cut into fragments of the same size and subcutaneously (s.c.) implanted into a new group of nude mice. The LC038 human lung cancer Patient Derived Xenograft (PDX) mice models were established in a similar manner. In brief, surgically removed tissues from the patients (FO) were cut into fragments of the same size and implanted into immunocompromised nude mice subcutaneously (F1 mice) within 2 hours after the surgery. When the xenograft tumors reached the size of 400-600 $mm^3$, they were excised, cut into fragments and implanted into nude mice for passage, which was F2, and so on.

Tumor nodules were measured in two dimensions with callipers and the tumor volume was calculated using the following formula: tumor volume=(length×width$^2$)×0.52. When the tumor volume reached 150~250 $mm^3$, tumor-bearing mice were randomized into treatment groups. Mice were then treated with either isotype controls (i.e. IgG1) or tested antibodies (i.e. FPA144, afhu21-26) once/twice a week from the day after randomisation. The tumor volume and body weight of the mice were measured twice weekly and the raw data were recorded. Tumor growth inhibition from start of treatment was assessed by comparing the mean change in tumor volume between the control and treated groups. The calculation was based on the geometric or arithmetic mean of relative tumor volume (RTV) in each group. RTV was calculated by dividing the tumor volume on the treatment day with the initial tumor volume.

Figure 10A:
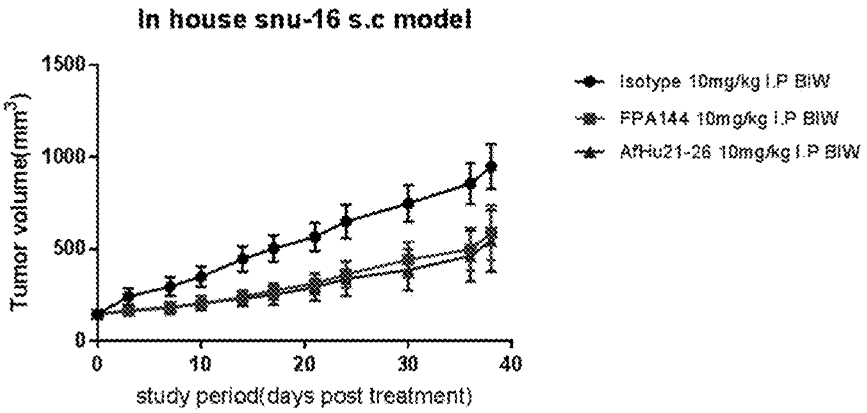
FIG. 10. In vivo antitumor efficacy of Ab afhu21-26 at 10 mg/kg i.p. dosed twice a week in a SNU16 gastric cancer xenograft model (A) and a LC038 patient-derived-xenograft lung cancer model (B). FPA144 used as comparison.
Figure 10B:
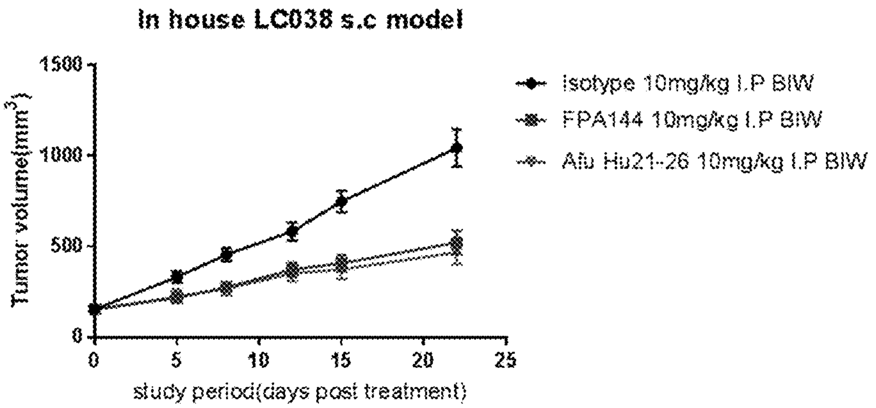

The in vivo tumor growth curve of SNU16 cells and LC038 PDX cells with afhu21-26 or the antibody FPA144 treatment were shown in FIGS. 10A and 10B, respectively. In both models, Afhu21-26 show better anti-tumor activity than the antibody FPA144. Similar results are also obtained for afhu21-21 as well.

Figure 11:
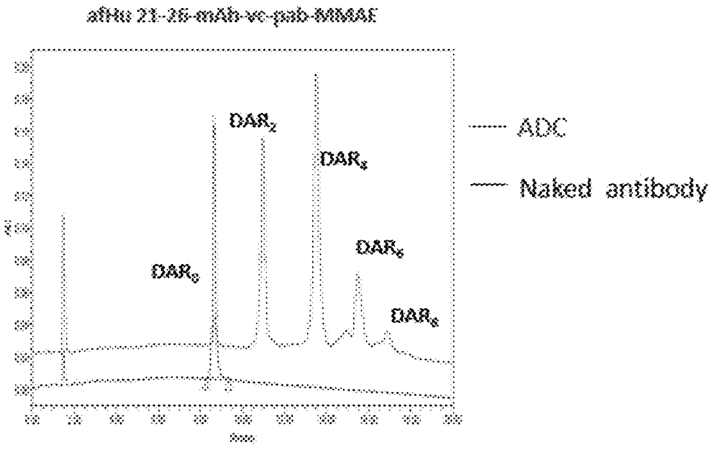
FIG. 11. Drug-Antibody-Ratio analysis of unconjugated afhu21-26 (bottom curve) and ADC conjugates afhu21-26-MMAE (top curve) using HIC-HPLC.

Example 8. Production of Antibody Drug Conjugates (ADC) and its Property 3 ml of Ab 21c at 10 mg/ml in PBS was added with fresh TCEP in molar ratio of TCEP/Ab of 2.2. After incubation in 37° C. water bath for 120 min, 1/10 (v/v) N,N-dimethylacetamide (DMA) was added into the antibody solution. Then 10 mM mc-vc-MMAE (mc=maleimidocaproyl; vc=valine-citrulline linker) in DMA was added into the Ab solution in molar ratio of MMAE to antibody of 6. The solution was kept at room temperature for overnight, and then equilibrate a PD-10 column with 25 ml 1×PBS. Then conjugation mixture was loaded to the PD-10 column to purify the ADC. The concentration of ADC was measured in Nanodrop. SEC-HPLC and HIC-HPLC was used for Quality Control analysis of aggregation of ADC and drug-antibody-ratio (DAR), respectively. The average DAR was calculated according to standard method. ADC conjugates 21c-MMAF and afhu21-26-MMAE were similarly generated. The HIC-HPLC histogram of afhu21-26-MMAE is shown in FIG. 11. The calculated DAR is 3.76, which is similar to the DAR of approved ADC drug Brentuximab vedotin.

Figure 12A:
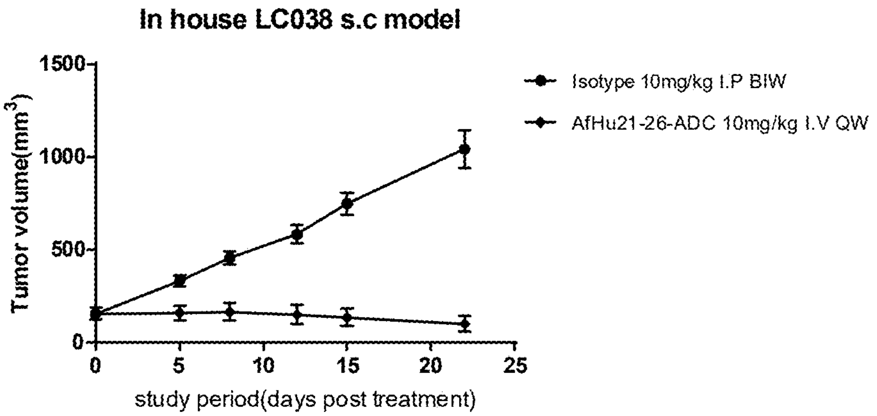
FIG. 12. In vivo antitumor efficacy of: (A) afhu21-26-MMAE in LC038 patient-derived-xenograft lung cancer model, and (B) of Ab 21c-MMAE, Ab 21c-MMAF in a SNU16 gastric cancer xenograft model. The animals were intravenously dosed weekly.
Figure 12B:
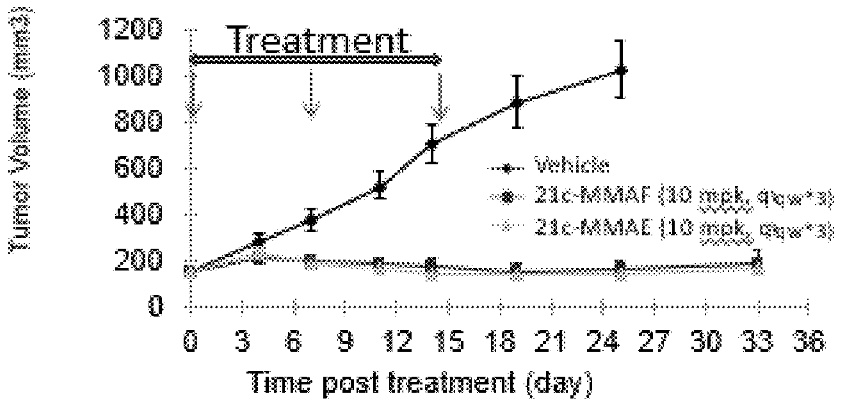

The anti-tumor activity of the ADC in various tumor xenograft models, such as LC038 PDX model and SNU16 xenograft were evaluated. Treatment with afHu21-26-MMAE, 21c-MMAF, and 21c-MMAE all induced tumor regression in both tumor models (FIGS. 12A and 12B).

What is claimed is:

1. An isolated antibody comprising:

(i) a heavy chain variable region (VH) comprising HCDR1, HCDR2 and HCDR3 sequences as set forth in SEQ ID NOs: 1, 3 and 5, respectively; and a light chain variable region (VL) comprising LCDR1, LCDR2 and LCDR3 sequences as set forth in SEQ ID NOs: 2, 4 and 6, respectively; or (ii) a heavy chain variable region (VH) comprising HCDR1, HCDR2 and HCDR3 sequences as set forth in SEQ ID NOs: 1, 7 and 5, respectively; and a light chain variable region (VL) comprising LCDR1, LCDR2 and LCDR3 sequences as set forth in SEQ ID NOs: 2, 4 and 6, respectively;

wherein the antibody is capable of specifically binding to both FGFR2b and FGFR1b, which does not have detectable binding affinity to FGFR2c.

2. The antibody of claim 1, wherein the heavy chain variable region comprising SEQ ID NOs: 8, 12, or 16 or a homologous sequence thereof having at least 80% sequence identity to SEQ ID NOs: 8, 12, or 16, wherein the homologous sequence has substitutions, insertions, or deletions occur in regions outside of the CDRs.

3. The antibody of claim 1, wherein the light chain variable region comprising SEQ ID NOs: 10 or 14 or a homologous sequence thereof having at least 80% sequence identity to SEQ ID NOs: 10 or 14, wherein the homologous sequence has substitutions, insertions, or deletions occur in regions outside of the CDRs.

4. The antibody of claim 1, wherein:

the heavy chain variable region comprising SEQ ID NO: 8 and the light chain variable region comprising SEQ ID NO: 10;

the heavy chain variable region comprising SEQ ID NO: 12 and the light chain variable region comprising SEQ ID NO: 14; or, the heavy chain variable region comprising SEQ ID NO: 16 and the light chain variable region comprising SEQ ID NO: 10.

5. The antibody of claim 1, further comprising one or more amino acid residue substitutions or modifications yet retains specific binding affinity to FGFR2b and/or to FGFR1b, wherein the substitutions or modifications are in the VH and/or VL sequences but outside any of the CDR sequences.

6. The antibody of claim 1, further comprising an immunoglobulin constant region.

7. The antibody of claim 6, wherein the constant region comprises one or more modifications of a native sequence which:

a) introduces or removes a glycosylation site, b) introduces a free cysteine residue, c) enhances binding to an activating Fc receptor compared to a constant region with native sequence, and/or d) enhances antibody-dependent cellular cytotoxicity (ADCC) compared to a constant region with native sequence.

8. The antibody of claim 7, which is glyco-engineered.

9. The antibody of claim 6, wherein the immunoglobulin constant region is a constant region of human immunoglobulin.

10. The antibody of claim 9, wherein the constant region of human immunoglobulin is a constant region of human IgG.

11. The antibody of claim 1, which is a chimeric antibody or a humanized antibody.

12. The antibody of claim 1, which is a diabody, a scFv, an scFv dimer, a bivalent ScFv (BsFv), a disulfide stabilized Fv fragment (dsFv), a $(dsFv)_2$, a bispecific dsFv (dsFv-dsFv'), an Fv fragment, a Fab, a Fab', a $F(ab')_2$, or a disulfide stabilized diabody (ds diabody).

13. The antibody of claim 1, capable of specifically binding to human FGFR2b, cynomolgus monkey FGFR2b, rat FGFR2b, and mouse FGFR2b.

14. The antibody of claim 1 linked to one or more conjugate moieties.

15. The antibody of claim 14, wherein the one or more conjugate moieties comprise a therapeutic agent, a radioactive isotope, a detectable label, a pharmacokinetic modifying moiety, or a purifying moiety.

16. The antibody of claim 15, wherein the one or more conjugate moieties are covalently attached either directly or via a linker.

17. The antibody of claim 14, wherein the one or more conjugate moieties are attached to specifically defined sites in the antibody via natural amino acids, unnatural amino acid, short peptide tags, or Asn297 glycans.

18. A pharmaceutical composition comprising the antibody of claim 1, and a pharmaceutically acceptable carrier.

19. A kit for detecting FGFR2b and/or FGFR1b, comprising the antibody of claim 1.

* * * * *

SEQUENCE LISTING

```
<160> NUMBER OF SEQ ID NOS: 21

<210> SEQ ID NO 1
<211> LENGTH: 5
<212> TYPE: PRT
<213> ORGANISM: mus musculus
```

<400> SEQUENCE: 1

Asn Tyr Trp Met His
1 5

<210> SEQ ID NO 2
<211> LENGTH: 10
<212> TYPE: PRT
<213> ORGANISM: mus musculus

<400> SEQUENCE: 2

Ser Ala Ser Ser Gly Leu Ser Tyr Met Ser
1 5 10

<210> SEQ ID NO 3
<211> LENGTH: 17
<212> TYPE: PRT
<213> ORGANISM: mus musculus

<400> SEQUENCE: 3

Ala Ile Tyr Pro Glu Asn Gly Asp Ile Asn Tyr Asn Gln Lys Phe Lys
1 5 10 15

Gly

<210> SEQ ID NO 4
<211> LENGTH: 7
<212> TYPE: PRT
<213> ORGANISM: mus musculus

<400> SEQUENCE: 4

Asp Thr Ser Asn Leu Ala Ser
1 5

<210> SEQ ID NO 5
<211> LENGTH: 4
<212> TYPE: PRT
<213> ORGANISM: mus musculus

<400> SEQUENCE: 5

Arg Gly Asp Tyr
1

<210> SEQ ID NO 6
<211> LENGTH: 9
<212> TYPE: PRT
<213> ORGANISM: mus musculus

<400> SEQUENCE: 6

Gln Gln Trp Ser Ser Tyr Pro Tyr Thr
1 5

<210> SEQ ID NO 7
<211> LENGTH: 17
<212> TYPE: PRT
<213> ORGANISM: Artificial Sequence
<220> FEATURE:
<223> OTHER INFORMATION: synthetic construct

<400> SEQUENCE: 7

Ala Ile Tyr Pro Glu Asn Arg Asp Ile Asn Tyr Asn Gln Lys Phe Lys
1 5 10 15

Gly

<210> SEQ ID NO 8
<211> LENGTH: 113
<212> TYPE: PRT
<213> ORGANISM: Artificial Sequence
<220> FEATURE:
<223> OTHER INFORMATION: synthetic construct

<400> SEQUENCE: 8

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Ile Tyr Pro Glu Asn Arg Asp Ile Asn Tyr Asn Gln Lys Phe
    50                  55                  60

Lys Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ser Arg Gly Asp Tyr Trp Gly Gln Gly Thr Thr Val Thr Val Ser
            100                 105                 110

Ser
```

<210> SEQ ID NO 9
<211> LENGTH: 339
<212> TYPE: DNA
<213> ORGANISM: Artificial Sequence
<220> FEATURE:
<223> OTHER INFORMATION: HUMANIZED 21-26 ANTIBODY HEAVY CHAIN VARIABLE
      REGION CODING SEQUENCE

<400> SEQUENCE: 9

```
gaggtgcagc tggtgcagag cggcgccgag gtgaagaagc ccggcgccag cgtgaaggtg      60

agctgcaagg ccagcggcta caccttcacc aactactgga tgcactgggt gaggcaggcc     120

cccggccagg gcctggagtg gatgggcgcc atctaccccg agaacaggga catcaactac     180

aaccagaagt tcaagggcag ggtgaccctg accagggaca ccagcatcag caccgcctac     240

atggagctga gcaggctgag gagcgacgac accgccgtgt actactgcac cagcaggggc     300

gactactggg gccagggcac caccgtgacc gtgagcagc                            339
```

<210> SEQ ID NO 10
<211> LENGTH: 106
<212> TYPE: PRT
<213> ORGANISM: Artificial Sequence
<220> FEATURE:
<223> OTHER INFORMATION: HUMANIZED 21-26/21-21 ANTIBODIES LIGHT CHAIN
      VARIABLE REGION AMINO ACID SEQUENCE

<400> SEQUENCE: 10

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Gly Leu Ser Tyr Met
            20                  25                  30

Ser Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
```

65 70 75 80

Asp Phe Ala Thr Tyr Tyr Cys Gln Gln Trp Ser Ser Tyr Pro Tyr Thr
85 90 95

Phe Gly Gln Gly Thr Lys Leu Glu Ile Lys
100 105

<210> SEQ ID NO 11
<211> LENGTH: 318
<212> TYPE: DNA
<213> ORGANISM: Artificial Sequence
<220> FEATURE:
<223> OTHER INFORMATION: HUMANIZED 21-26/21-21 ANTIBODIES LIGHT CHAIN VARIABLE REGION CODING SEQUENCE

<400> SEQUENCE: 11
gccatccagc tgacccagag ccccagcagc ctgagcgcca gcgtgggcga cagggtgacc 60
atcacctgca gcgccagcag cggcctgagc tacatgagct ggtaccagca gaagcccggc 120
aaggccccca agctgctgat ctacgacacc agcaacctgg ccagcggcgt gcccagcagg 180
ttcagcggca gcggcagcgg caccgacttc accctgacca tcagcagcct gcagcccgag 240
gacttcgcca cctactactg ccagcagtgg agcagctacc cctacacctt cggccagggc 300
accaagctgg agatcaag 318

<210> SEQ ID NO 12
<211> LENGTH: 113
<212> TYPE: PRT
<213> ORGANISM: Artificial Sequence
<220> FEATURE:
<223> OTHER INFORMATION: CHIMERIC 21 ANTIBODY HEAVY CHAIN VARIABLE REGION AMINO ACID SEQUENCE

<400> SEQUENCE: 12

Glu Val Gln Leu His Gln Ser Gly Thr Val Leu Ala Arg Pro Gly Ala
1 5 10 15

Ser Val Lys Met Ser Cys Lys Thr Ser Gly Tyr Thr Phe Thr Asn Tyr
20 25 30

Trp Met His Trp Ile Lys Gln Arg Pro Gly Gln Gly Leu Glu Trp Ile
35 40 45

Gly Ala Ile Tyr Pro Glu Asn Gly Asp Ile Asn Tyr Asn Gln Lys Phe
50 55 60

Lys Gly Lys Ala Lys Leu Thr Ala Val Thr Ser Ala Ser Thr Ala Tyr
65 70 75 80

Met Asp Leu Ser Ser Leu Thr Asn Glu Asp Ser Ala Val Tyr Tyr Cys
85 90 95

Thr Ser Arg Gly Asp Tyr Trp Gly Gln Gly Thr Thr Leu Thr Val Ser
100 105 110

Ser

<210> SEQ ID NO 13
<211> LENGTH: 339
<212> TYPE: DNA
<213> ORGANISM: Artificial Sequence
<220> FEATURE:
<223> OTHER INFORMATION: CHIMERIC 21 ANTIBODY HEAVY CHAIN VARIABLE REGION CODING SEQUENCE

<400> SEQUENCE: 13
gaggttcagc tccaccagtc tgggactgtg ctggcaaggc ctggggcttc agtgaagatg 60
tcctgcaaga cttctggcta cacatttacc aactactgga tgcactggat aaaacagagg 120
cctggacagg gtctggaatg gataggggct atttatcctg aaaatggtga tattaactac 180
aaccagaagt tcaagggcaa ggccaaactg actgcagtca catccgccag cactgcctac 240
atggacctca gcagcctgac aaatgaggac tctgcggtct attactgtac aagtcggggg 300
gactactggg gccaaggcac cactctcaca gtctcctca 339

<210> SEQ ID NO 14
<211> LENGTH: 106
<212> TYPE: PRT
<213> ORGANISM: Artificial Sequence
<220> FEATURE:
<223> OTHER INFORMATION: CHIMERIC 21 ANTIBODY LIGHT CHAIN VARIABLE
REGION AMINO ACID SEQUENCE

<400> SEQUENCE: 14

Gln Ile Val Leu Thr Gln Ser Pro Ala Ile Met Ser Ala Ser Pro Gly
1 5 10 15

Glu Lys Val Thr Met Thr Cys Ser Ala Ser Ser Gly Leu Ser Tyr Met
20 25 30

Ser Trp Tyr Gln Gln Lys Pro Gly Ser Ser Pro Arg Leu Leu Ile Tyr
35 40 45

Asp Thr Ser Asn Leu Ala Ser Gly Val Pro Val Arg Phe Ser Gly Ser
50 55 60

Gly Ser Gly Thr Ser Tyr Ser Leu Thr Ile Ser Arg Met Glu Ala Glu
65 70 75 80

Asp Ala Ala Thr Tyr Tyr Cys Gln Gln Trp Ser Ser Tyr Pro Tyr Thr
85 90 95

Phe Gly Gly Gly Thr Lys Leu Glu Ile Lys
100 105

<210> SEQ ID NO 15
<211> LENGTH: 318
<212> TYPE: DNA
<213> ORGANISM: Artificial Sequence
<220> FEATURE:
<223> OTHER INFORMATION: CHIMERIC 21 ANTIBODY LIGHT CHAIN VARIABLE
REGION CODING SEQUENCE

<400> SEQUENCE: 15
caaattgttc tcacccagtc tccagcaatc atgtctgcat ctccagggga gaaggtcacc 60
atgacctgca gtgccagctc aggtttaagt tacatgtcct ggtaccagca gaagccagga 120
tcctccccca gactcctgat ttatgacaca tccaacctgg cttctggagt ccctgttcgc 180
ttcagtggca gtgggtctgg gacctcttac tctctcacaa tcagccgaat ggaggctgaa 240
gatgctgcca cttattactg ccagcagtgg agtagttacc cgtacacgtt cggagggggg 300
accaagctgg aaataaaa 318

<210> SEQ ID NO 16
<211> LENGTH: 113
<212> TYPE: PRT
<213> ORGANISM: Artificial Sequence
<220> FEATURE:
<223> OTHER INFORMATION: HUMANIZED 21-21 ANTIBODY HEAVY CHAIN VARIABLE
REGION AMINO ACID SEQUENCE

<400> SEQUENCE: 16

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr

```
            20                  25                  30

Trp Met His Trp Val Arg Gln Ala Pro Gly Gln Gly Leu Glu Trp Met
        35                  40                  45

Gly Ala Ile Tyr Pro Glu Asn Gly Asp Ile Asn Tyr Asn Gln Lys Phe
    50                  55                  60

Lys Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ser Arg Gly Asp Tyr Trp Gly Gln Gly Thr Thr Val Thr Val Ser
            100                 105                 110

Ser


<210> SEQ ID NO 17
<211> LENGTH: 339
<212> TYPE: DNA
<213> ORGANISM: Artificial Sequence
<220> FEATURE:
<223> OTHER INFORMATION: HUMANIZED 21-21 ANTIBODY HEAVY CHAIN VARIABLE
      REGION CODING SEQUENCE

<400> SEQUENCE: 17

gaggtgcagc tggtgcagag cggcgccgag gtgaagaagc ccggcgccag cgtgaaggtg     60

agctgcaagg ccagcggcta caccttcacc aactactgga tgcactgggt gaggcaggcc    120

cccggccagg gcctggagtg gatgggcgcc atctaccccg agaacggcga catcaactac    180

aaccagaagt tcaagggcag ggtgaccctg accagggaca ccagcatcag caccgcctac    240

atggagctga gcaggctgag gagcgacgac accgccgtgt actactgcac cagcaggggc    300

gactactggg gccagggcac caccgtgacc gtgagcagc                           339


<210> SEQ ID NO 18
<211> LENGTH: 213
<212> TYPE: PRT
<213> ORGANISM: Artificial Sequence
<220> FEATURE:
<223> OTHER INFORMATION: HUMANIZED 21-26 ANTIBODY LIGHT CHAIN AMINO ACID
      SEQUENCE

<400> SEQUENCE: 18

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Gly Leu Ser Tyr Met
            20                  25                  30

Ser Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 19
<211> LENGTH: 443
<212> TYPE: PRT
<213> ORGANISM: Artificial Sequence
<220> FEATURE:
<223> OTHER INFORMATION: HUMANIZED 21-26 ANTIBODY HEAVY CHAIN AMINO ACID
      SEQUENCE

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Ile Tyr Pro Glu Asn Arg Asp Ile Asn Tyr Asn Gln Lys Phe
    50                  55                  60

Lys Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ser Arg Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
```

```
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440


<210> SEQ ID NO 20
<211> LENGTH: 213
<212> TYPE: PRT
<213> ORGANISM: Artificial Sequence
<220> FEATURE:
<223> OTHER INFORMATION: synthetic construct

<400> SEQUENCE: 20

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Gly Leu Ser Tyr Met
            20                  25                  30

Ser Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

```
        195                 200                 205

Asn Arg Gly Glu Cys
    210


<210> SEQ ID NO 21
<211> LENGTH: 443
<212> TYPE: PRT
<213> ORGANISM: Artificial Sequence
<220> FEATURE:
<223> OTHER INFORMATION: synthetic construct

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Ile Tyr Pro Glu Asn Arg Asp Ile Asn Tyr Asn Gln Lys Phe
    50                  55                  60

Lys Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ser Arg Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
```

-continued

```
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440
```